US012629151B2

(12) United States Patent
Mitchell et al.

(10) Patent No.: US 12,629,151 B2
(45) Date of Patent: May 19, 2026

(54) DEVICE AND ASSEMBLY FOR TISSUE ATTACHMENT

(71) Applicants: The Regents of the University of Colorado, a body corporate, Denver, CO (US); ConneX BioMedical, Inc., Aurora, CO (US)

(72) Inventors: Max Bannister Mitchell, Castle Pines, CO (US); Jeremy H. Morgan, Missoula, MT (US); Jeffery N. Steinmetz, Arvada, CO (US); Dan Sims, Arvada, CO (US); Christopher E. Banas, Breckenridge, CO (US)

(73) Assignee: Connex Biomedical, Inc., Aurora, CO (US)

( * ) Notice: Subject to any disclaimer, the term of this patent is extended or adjusted under 35 U.S.C. 154(b) by 0 days.

(21) Appl. No.: 18/458,398

(22) Filed: Aug. 30, 2023

(65) Prior Publication Data

US 2024/0016495 A1 Jan. 18, 2024

Related U.S. Application Data

(63) Continuation-in-part of application No. 18/188,393, filed on Mar. 22, 2023, and a continuation-in-part of
(Continued)

(51) Int. Cl.
*A61B 17/11* (2006.01)
*A61B 17/00* (2006.01)
(Continued)

(52) U.S. Cl.
CPC ..... *A61B 17/11* (2013.01); *A61B 2017/00893* (2013.01); *A61B 2017/1107* (2013.01);
(Continued)

(58) Field of Classification Search
CPC ............ A61B 17/11; A61B 2017/1107; A61B 2017/1135; A61B 2017/1103;
(Continued)

(56) References Cited

U.S. PATENT DOCUMENTS 5,234,447 A * 8/1993 Kaster ................... A61B 17/11
606/151
5,700,285 A 12/1997 Myers et al.
(Continued)

FOREIGN PATENT DOCUMENTS

DE 19936120 A1 7/1999
EP 201266628 A2 12/2002
(Continued)

OTHER PUBLICATIONS

Notification of Transmittal of the International Search Report and the Written Opinion of the International Searching Authority, or the Declaration. International Application No. PCT/US2023/064833. Dated Jun. 21, 2023.
(Continued)

*Primary Examiner* — Jing Rui Ou
(74) *Attorney, Agent, or Firm* — Rosenbaum IP, P.C.; David G. Rosenbaum

(57) ABSTRACT

An assembly and method for end-to-side connection to anatomical tissue is disclosed. The system and method are particularly useful in coupling a ventricular assist device pump to an aorta. The assembly and method include using a tubular graft member coupled to a connection ring having at least one of a plurality of distally projecting tines extending from a distal aspect of the connection ring, and a stent having a distal flange section configured to abut an abluminal wall surface of the aorta, and an assembly including the tubular graft member and connection ring, for delivering the end-to-side connection.

15 Claims, 18 Drawing Sheets

Related U.S. Application Data application No. 18/188,390, filed on Mar. 22, 2023, and a continuation-in-part of application No. 16/739,807, filed on Jan. 10, 2020, now Pat. No. 11,974,748.

(51) Int. Cl.
| | |
|---|---|
| *A61M 60/178* | (2021.01) |
| *A61M 60/861* | (2021.01) |

(52) U.S. Cl.
CPC .... *A61B 2017/1135* (2013.01); *A61M 60/178* (2021.01); *A61M 60/861* (2021.01)

(58) Field of Classification Search
CPC .... A61B 2017/1132; A61B 2017/1139; A61B 2017/00893; A61M 60/178; A61M 60/861
See application file for complete search history.

(56) References Cited

U.S. PATENT DOCUMENTS

| | | | |
|---|---|---|---|
| 6,113,612 A * | 9/2000 | Swanson .................. | A61F 2/88 623/1.15 |
| 6,190,590 B1 | 2/2001 | Randall et al. | |
| 6,203,735 B1 | 3/2001 | Edwin et al. | |
| 6,273,912 B1 | 8/2001 | Scholz et al. | |
| 6,383,214 B1 | 5/2002 | Banas et al. | |
| 6,652,578 B2 | 11/2003 | Bailey et al. | |
| 7,794,471 B1 | 9/2010 | Bender et al. | |
| 9,445,886 B2 | 9/2016 | Harris et al. | |
| 10,335,527 B2 | 7/2019 | Mitchell et al. | |
| 2001/0029383 A1 | 10/2001 | Solem | |
| 2001/0041902 A1 | 11/2001 | Lepulu et al. | |
| 2002/0082627 A1 * | 6/2002 | Berg ...................... | A61F 2/064 606/155 |
| 2003/0023251 A1 * | 1/2003 | Gifford, III ......... | A61B 17/115 606/153 |
| 2004/0210244 A1 * | 10/2004 | Vargas ............. | A61B 17/32053 606/151 |
| 2005/0192604 A1 | 9/2005 | Carson et al. | |
| 2006/0025790 A1 * | 2/2006 | de Winter .............. | A61B 17/11 606/153 |
| 2008/0009936 A1 * | 1/2008 | Kim ....................... | A61B 17/11 623/1.15 |
| 2008/0109019 A1 * | 5/2008 | Tulleken ................ | A61B 17/11 206/570 |
| 2010/0023132 A1 * | 1/2010 | Imran ................. | A61B 17/1114 623/23.72 |
| 2010/0130995 A1 | 5/2010 | Yevzlin et al. | |
| 2010/0161040 A1 | 6/2010 | Braido et al. | |
| 2011/0118764 A1 | 5/2011 | Beane et al. | |
| 2012/0296151 A1 | 11/2012 | Curtis et al. | |
| 2014/0343582 A1 | 11/2014 | Asfora et al. | |
| 2015/0012006 A1 | 1/2015 | Hausen et al. | |
| 2021/0077186 A1 * | 3/2021 | Pate .................. | A61B 18/1492 |

FOREIGN PATENT DOCUMENTS

| | | |
|---|---|---|
| WO | 199300868 | 1/1993 |
| WO | 199728749 | 8/1997 |
| WO | 200100108 A1 | 1/2001 |
| WO | 200234143 A1 | 5/2002 |

OTHER PUBLICATIONS

International Search Report. International Application No. PCT/US2023/064833. Dated Jun. 21, 2023.
Written Opinion of the International Searching Authority. International Application No. PCT/US2023/064833. Dated Jun. 21, 2023.
Written Opinion of the International Searching Authority. International Application No. PCT/US2020/013135. Dated Jul. 16, 2020.
International Search Report. International Application No. PCT/US2020/013135. Dated Jul. 16, 2020.

* cited by examiner

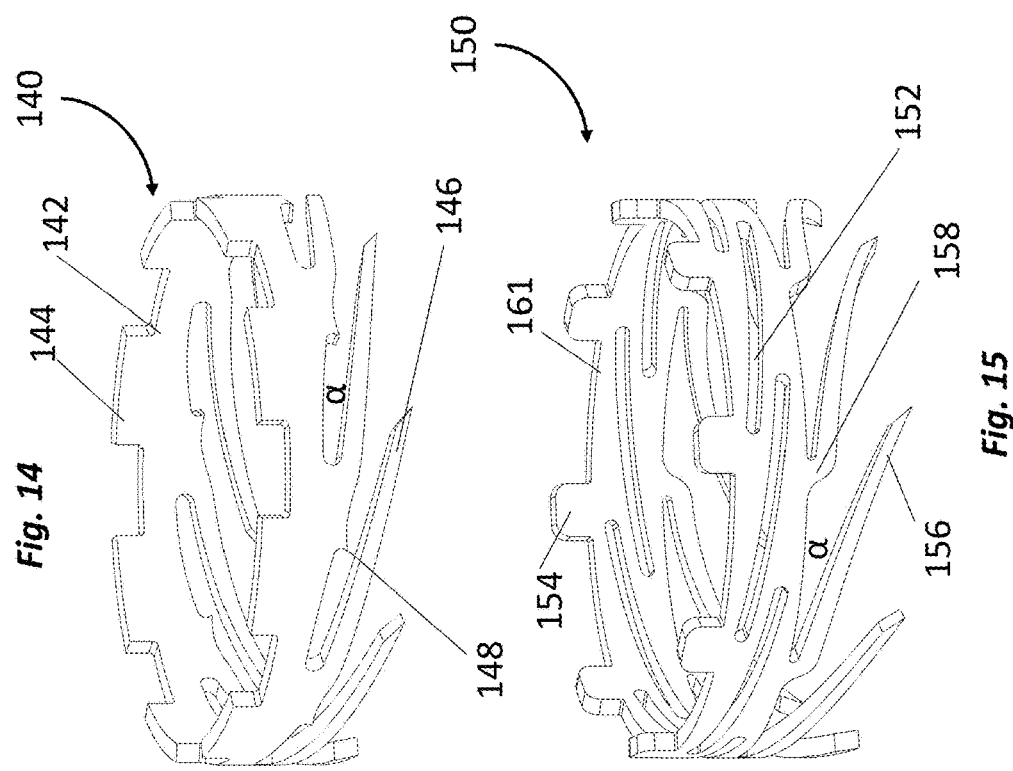
Fig. 14
Fig. 15
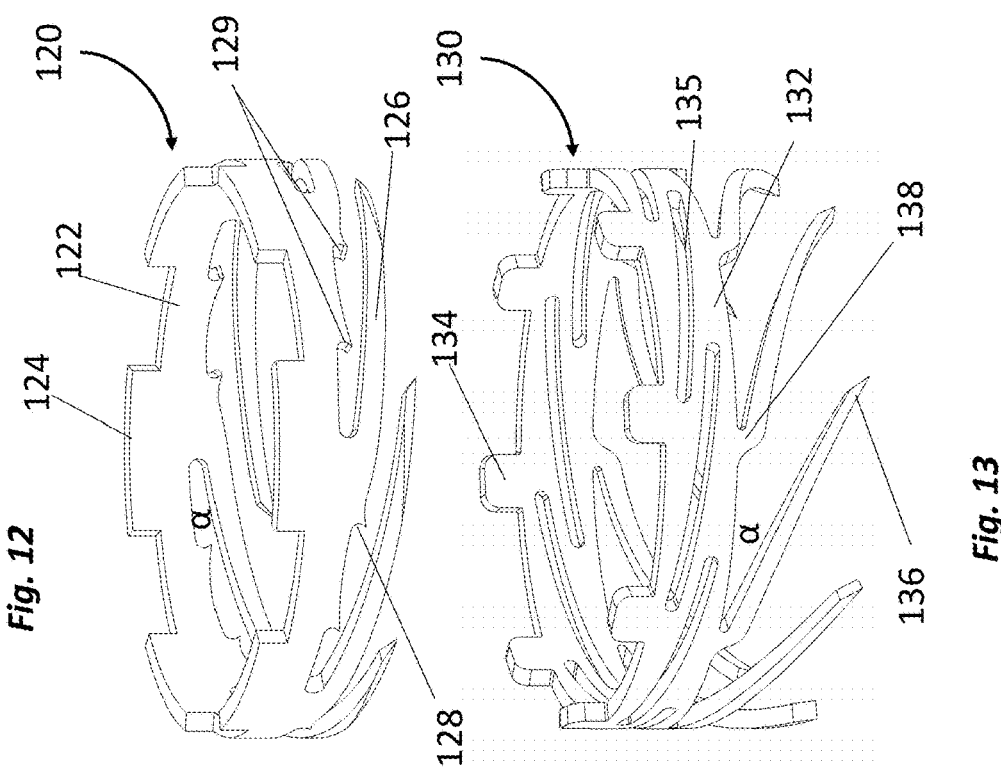
Fig. 12
Fig. 13

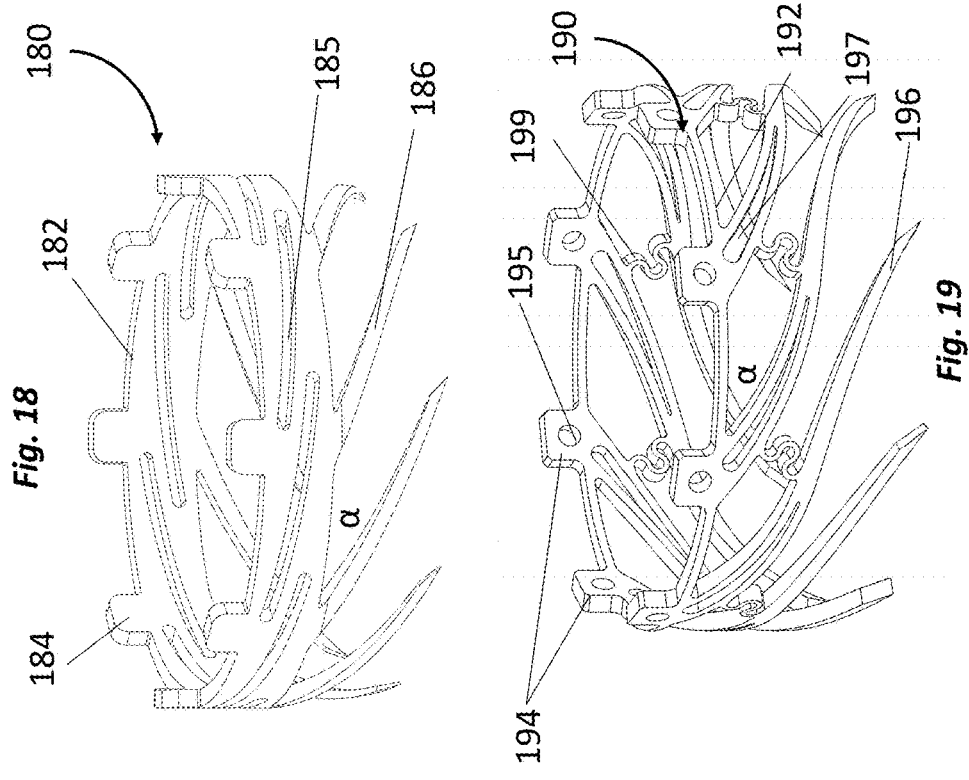
Fig. 18
Fig. 19
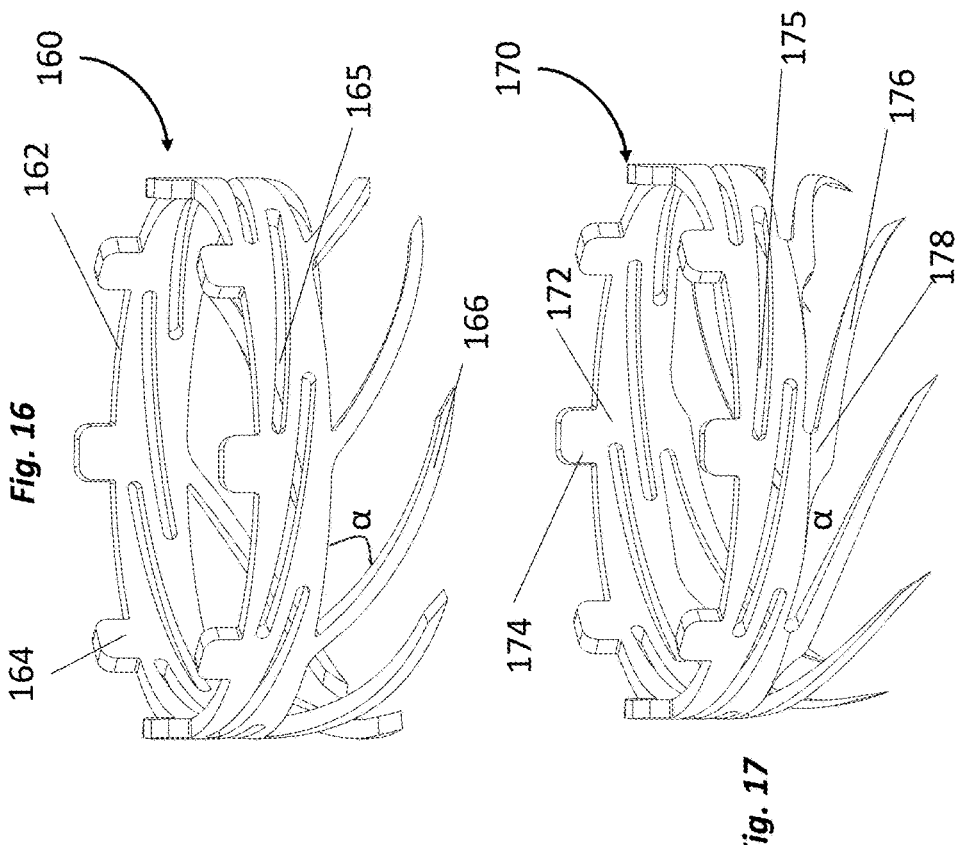
Fig. 16
Fig. 17

400

422    420    418    416    414    412    410

DEVICE AND ASSEMBLY FOR TISSUE ATTACHMENT

CROSS-REFERENCE TO RELATED APPLICATIONS

This application is related to and is a continuation-in-part of co-pending U.S. patent application Ser. No. 18/188,390 filed Mar. 22, 2023, is a continuation-in-part of co-pending U.S. patent application Ser. No. 18/188,393 filed Mar. 22, 2023, and is a continuation-in-part of co-pending U.S. patent application Ser. No. 16/739,807, filed Aug. 12, 2020.

BACKGROUND OF THE INVENTION

The present invention pertains generally to devices and methods for joining an anatomic tissue either to other anatomic tissue or to tubular conduits. Non-limiting examples of uses of the inventive devices and methods include end-to-side anastomosis of a tubular conduit with an anatomic passageway, and/or synthetic or biological graft fixation to soft or hard tissues. Examples of anatomic passageways for which end-to-side anastomosis may be created using the devices and methods of the present disclosure, include, without limitation, blood vessels, lymph ducts, trachea or other airway, esophagus, stomach, small or large intestine, and chambered organs, such as the heart, kidney, or brain.

More particularly, the present invention relates to an assembly for creating an end-to-side anastomosis between a tubular conduit and a portion of the anatomic passageway, such, for example, the aorta or other major blood vessel. Still more particularly, the present invention pertains to an attachment device for coupling an end of the tubular conduit to the side of a portion of the anatomic passageway. Further, the present invention pertains to an assembly that generally includes the attachment device, a graft component, a graft delivery component, a coring component for forming a tissue core plug, securing the tissue core plug, and removing the tissue core plug, and a stent that nests against a luminal wall surface of the graft component as well as the luminal wall surface of the anatomic passageway.

For purposes of clarity and by way of non-limiting example only, reference to a major blood vessel, such as the aorta, may be made herein as an example of an anatomic tissue or passageway onto and into which the assemblies described herein may be deployed.

The attachment device consists generally of an annular ring having a plurality of helically oriented tines projecting axially from a distal end of the annular ring and a plurality of engagement members at a proximal end of the annular ring. The annular ring may be a unitary ring, or a segmented ring. Where a segmented annular ring is employed, it may be comprised of plural arcuate sections arranged to form a substantially annular ring structure. The plural arcuate sections may be configured to interface with one another in a reciprocally slidable arrangement, an articulating arrangement, or other arrangement where individual or groups of arcuate sections are movable relative to other arcuate sections of the annular ring. The annular ring may further include more than one annular ring structures with each annular ring having helically oriented tines that are oriented in counter-rotating fashion relative to the other annular ring structure. Alternatively, where more than one annular ring is employed, the lengths, configuration, shape, rotational orientation, angles, or spacing of the helically oriented tines may be different in a first annular ring than in a second annular ring.

The graft component is a pliable or semi-pliable tubular graft having a central lumen that opens at proximal and distal ends of the graft. The graft component may, optionally, have alignment indicia marked thereupon.

The graft delivery component is a tool that includes an axial compression sleeve and a driver for rotating the attachment device and graft component to embed the helically oriented tines of the graft component into the anatomic tissue. The axial compression sleeve is longitudinally translatable relative to the driver, the graft component, and the attachment device, and is extensible beyond the distal end of the attachment device to axially compress the anatomic tissue and create a substantially planar surface on the anatomic tissue to engage the helically oriented tines into.

The coring component is a tool that includes a stabilization device and a core cutting device. The stabilization device includes a stabilization tubular member having a handle at a proximal end and a coring retention member at a distal end of the stabilization tubular member. The core cutting device includes a coring tubular member having a handle at a proximal end thereof and a core cutting member at a distal end of the coring tubular member. Optionally a flushing port may be provided in either the coring tubular member or the coring tubular member handle. Further, a set screw and set screw receiver opening may be provided in the coring tubular member or the coring tubular member handle to prevent undesired rotation of the core cutting device. The coring retention member penetrates into the anatomical tissue and may be rotated to cut a tissue plug from the anatomic tissue, with the tissue plug being retained on the coring retention member at the distal end of the stabilization tubular member.

The stent component includes a stent having a collapsed state and an expanded state, and having a distal circumferential flange that extends radially outward away from a central longitudinal axis of the stent when the distal circumferential flange is in the expanded state. The stent consists generally of a tubular proximal section and the distal circumferential flange at a distal portion of the stent. As is known in the stent arts, the stent of the stent component may have many different structural geometries. That is that the stent may be made of a single or plural materials, may be made of a single hypotube that is machined into structural members that form the wall surfaces of the stent, may be made balloon-expandable or self-expanding, in whole or in part, may optionally include radiopaque markers, may optionally include drug-eluting capabilities, or such other structural and/or functional features as are known in the stent arts.

The stent may, optionally, be further covered by or encapsulated with, in whole or in part, a graft covering that covers the luminal wall surface and/or abluminal wall surface of the stent. Where provided, the graft covering may cover only the proximal tubular section, only the distal circumferential flange, or both the proximal tubular section and the distal circumferential flange. Where provided, the graft covering preferably extends about an entire circumferential aspect of the portion or portions of the stent which it covers or encapsulates.

The stent component further includes a delivery system for the stent. The stent delivery system may have a stent retaining sleeve from which the stent is deployed by translating the stent relative to the retaining sleeve to impart a controlled release of the distal circumferential flange section separately from the proximal tubular section of the stent. Optionally, the stent delivery system further includes a proximal retention member that is removably coupled with and releasable from a proximal end of the proximal tubular section; the proximal retention member may, optionally, be configured to seal a central lumen of the proximal tubular section in order to prevent fluid flow through the central lumen during the delivery process and maintain a degree of hemostasis. The proximal retention member may be configured in a wide number of ways to both removably couple to the proximal tubular section of the stent, release the stent, and maintain a degree of hemostasis by sealing the proximal tubular section of the stent until the stent is released from the proximal retention member. An example of one configuration of the proximal retention member is to provide a sealing device such as that described in U.S. Pat. No. 9,345,461 in which a coiled sealing element is made of a coiled string element that is engaged with the proximal tubular section of the stent to seal the stent lumen. Once the proximal tubular section of the stent is positioned, the coiled string element is withdrawn, unwinding the coiled string element and deploying the tubular portion of the stent, releasing the seal provided by the sealing device and opening the stent lumen. It will be appreciated by those in the art that various other methods of providing a releasable sealing element in conjunction with the proximal tubular section of the stent are intended and contemplated by the present disclosure.

In one example of an application of the end-to-side anastomosis assembly, the assembly has particular application in coupling an outflow of a circulatory assist device. Examples of circulatory assist devices are ventricular assist devices ("VAD") and left ventricular assist device ("LVAD") that pump blood from the heart and create a blood flow path from the pump to the aorta. It will be understood that the end-to-side anastomosis assembly has other non-vascular medical applications to anatomic passageways. Additionally, non-medical applications of the devices and methods are also intended and contemplated by the present disclosure. Further, reference to the medical application of the devices and methods of the present disclosure to circulatory assist devices, such as VADs or LVADs devices, is intended to be a non-limiting example of an application of the devices and methods described herein.

Heart failure is a leading cause of death in developed countries. An estimated 100,000 Americans develop end-stage congestive heart failure each year with a one-year mortality of approximately 50%. There are many etiologies of heart failure. Treatment options depend on the underlying cause and consist of drug therapy, catheter based or surgical interventions for coronary artery disease, and catheter or surgical procedures for valve disease and other lesions.

In the past, the only treatment for end-stage non-correctable heart failure was heart transplantation. Approximately 4,200 heart transplant procedures are performed annually in the United States and approximately 7,500 are performed annually world-wide. At any given time, there are approximately 3,000 patients on the heart transplant waiting list in the United States. Consequently, demand for transplantation far outstrips the supply of donor hearts, and it is unlikely that this supply imbalance will improve. Because of the donor supply imbalance, practitioners have developed mechanical VAD systems to support the circulation in patients with heart failure.

Initially, VAD therapy was limited to heart transplant candidates and was intended to bridge patients to heart transplant and improve their baseline health status going into transplant. This strategy is commonly referred to as Bridge to Transplant ("BTT"). As technology improved, VAD outcomes improved, and VAD therapy was extended to the larger population of heart failure patients who are not candidates for transplant. VAD treatment in the latter pool of patients is referred to as Destination Treatment ("DT"). Most patients, regardless of treatment intent, can be supported with a left sided device alone.

The current generation of LVADs in common use are continuous flow devices. The newer continuous flow LVADs are small enough to be implanted entirely within the pericardial space and do not require an intra-abdominal pocket. In general, the pumping inlet mechanism of current LVADs is surgically attached directly to a heart chamber. The outflow end of the pumping mechanism consists of a prosthetic vascular tube graft that is sewn end to side to a major artery—usually the aorta. There are other surgical indications for the attachment of the end of a large prosthetic vascular graft to the side of a major artery. For example, aorta to aorta bypass procedures require end-to-side attachment of a prosthetic graft to the aorta at one end and the aorta at the other end. An alternative example of an application for the end-to-side anastomosis system is in implanting an apical-aortic valve conduit in which a valved conduit is implanted into the left ventricular apex and then a distal end of the valved conduit is joined by an end-to-side anastomosis to the aorta bypassing the aortic valve.

Conventional methods for the surgical attachment, e.g., anastomosis, of the end of a large prosthetic tube graft to the side of a major artery typically involve isolating a segment of the target artery with a side-biting clamp or between two completely occlusive clamps. An opening is created in the target artery, known as an arteriotomy, and the prosthetic tube graft is manually sutured to the arteriotomy in an end to side manner with the arteriotomy opening and a central lumen of the prosthetic tube graft being in fluid flow communication with each other. Suturing methods vary and include running suture techniques, interrupted suture techniques, i.e., using a plurality of individually placed and tied sutures, or a combination of these methods. Conventional suturing methods are time consuming, require clamping of the target vessel which in some cases may be diseased, and can be associated with suture hole bleeding due to suture hole elongation. In contrast, by eliminating the suturing, the assembly of the present disclosure improves hemostasis decreases procedure time, standardizes the procedure so that it is not dependent upon a surgeon's technical abilities, and will facilitate the use of minimally invasive incisions for surgical access to the site for the end-to-side anastomosis.

While the present invention will be described with respect to its use with a VAD procedure and system, those skilled in the art will understand and appreciate that the scope of the present invention is intended not to be limited to VAD procedures and systems but to end-to-side connections between tubular medical grafts, autologous anatomical tubular grafts, heterologous or other biological tubular grafts, and other anatomical structures, such as the gastrointestinal system, biliary system, lymphatic system, urinary system or the like.

SUMMARY OF THE INVENTION

The currently disclosed devices, assemblies, and method for making an end-to-side connection are well suited to forming attachments between a tubular conduit and an anatomic passageway, such as a major blood vessel.

As a non-limiting example of a use of the disclosed assemblies, there is provided an end-to-side connection assembly configured to be coupled to a wall of a large blood vessel, such as the aorta, to direct blood flow into the vessel or provide access to the lumen of the blood vessel.

Other non-limiting examples may include use of the end-to-side connection assembly to couple other anatomic passageways, such as the small intestine, large intestine, stomach, or rectum, bile ducts, or the like.

It is, therefore, an objective of the present disclosure to provide a connection assembly particularly suited from end-to-side connection of anatomic tissue to other anatomic tissue or the end-to-side connection of anatomic tissue to synthetic or biological tissue.

It is a further objective of the present disclosure to provide an end-to-side connection assembly consisting generally of the attachment device, the graft component, the graft delivery component, the coring component, and the stent component, as described above.

It is yet a further objective of the present disclosure to provide an end-to-side connection assembly that is particularly well suited for connecting an end of a tubular conduit to a side wall of another tubular conduit to establish a fluid flow connection therebetween.

It is still another objective of the present disclosure to provide an end-to-side connection assembly in which the end-to-side connection is initially made between a tubular conduit and the side wall of another tubular conduit by providing a tubular graft member having an annular ring member with helically oriented tines projecting from a distal end of the annular ring member.

It is yet still another objective of the present disclosure that the tubular graft member has a distal end that projects distally from the distal end of the annular ring member.

It is still a further objective of the present disclosure that the distal end of the tubular graft member that projects distally from the distal end of the annular ring member is configured to axially compress against the anatomic tissue and assist in imparting a fluid tight seal between the tubular graft member and the anatomic tissue.

It is yet still another objective of the present disclosure that the fluid tight seal between the tubular graft member and the anatomic tissue occurs without sutures, sewing rings, pledgets, or other compression or closure devices.

It is yet a further objective of the present disclosure to provide an end-to-side anastomosis assembly having an axial compression component that is deployable to axially compress anatomical tissue to provide a tissue surface that is flattened to receive and engage with the annular ring member.

It is still another objective of the present disclosure to provide various embodiments of the annular ring member.

It is still another further objective of the present disclosure to provide a stabilization component that operates in conjunction with a coring component to capture a portion of anatomic tissue in the stabilization component then core the anatomic tissue such that the cored tissue is captured on the stabilization component for removal from the body.

It is yet still another further objective of present disclosure to provide a stent and a stent delivery system that is configured to pass through the central lumen of the tubular graft member and deploy a distal circumferential flange of the stent member on an opposing wall surface of the anatomic tissue from the annular ring member, and then engage a proximal portion of the stent member within the central lumen of the tubular graft member to assist in retaining the tubular graft member and annular ring member in the anatomic tissue.

BRIEF DESCRIPTION OF THE DRAWINGS

FIG. 12 is a perspective diagrammatic view of a first variant of an attachment device in accordance with the present invention.

FIG. 13 is a perspective diagrammatic view of a second variant of an attachment device in accordance with the present invention.

FIG. 14 is a perspective diagrammatic view of a third variant of an attachment device in accordance with the present invention.

FIG. 15 is a perspective diagrammatic view of a fourth variant of an attachment device in accordance with the present invention.

FIG. 16 is a perspective diagrammatic view of a fifth variant of an attachment device in accordance with the present invention.

FIG. 17 is a perspective diagrammatic view of a sixth variant of an attachment device in accordance with the present invention.

FIG. 18 is a perspective diagrammatic view of a seventh variant of an attachment device in accordance with the present invention.

FIG. 19 is a perspective diagrammatic view of a eighth variant of an attachment device in accordance with the present invention.

DETAILED DESCRIPTION OF THE PREFERRED EMBODIMENTS

Figures 1, 3:
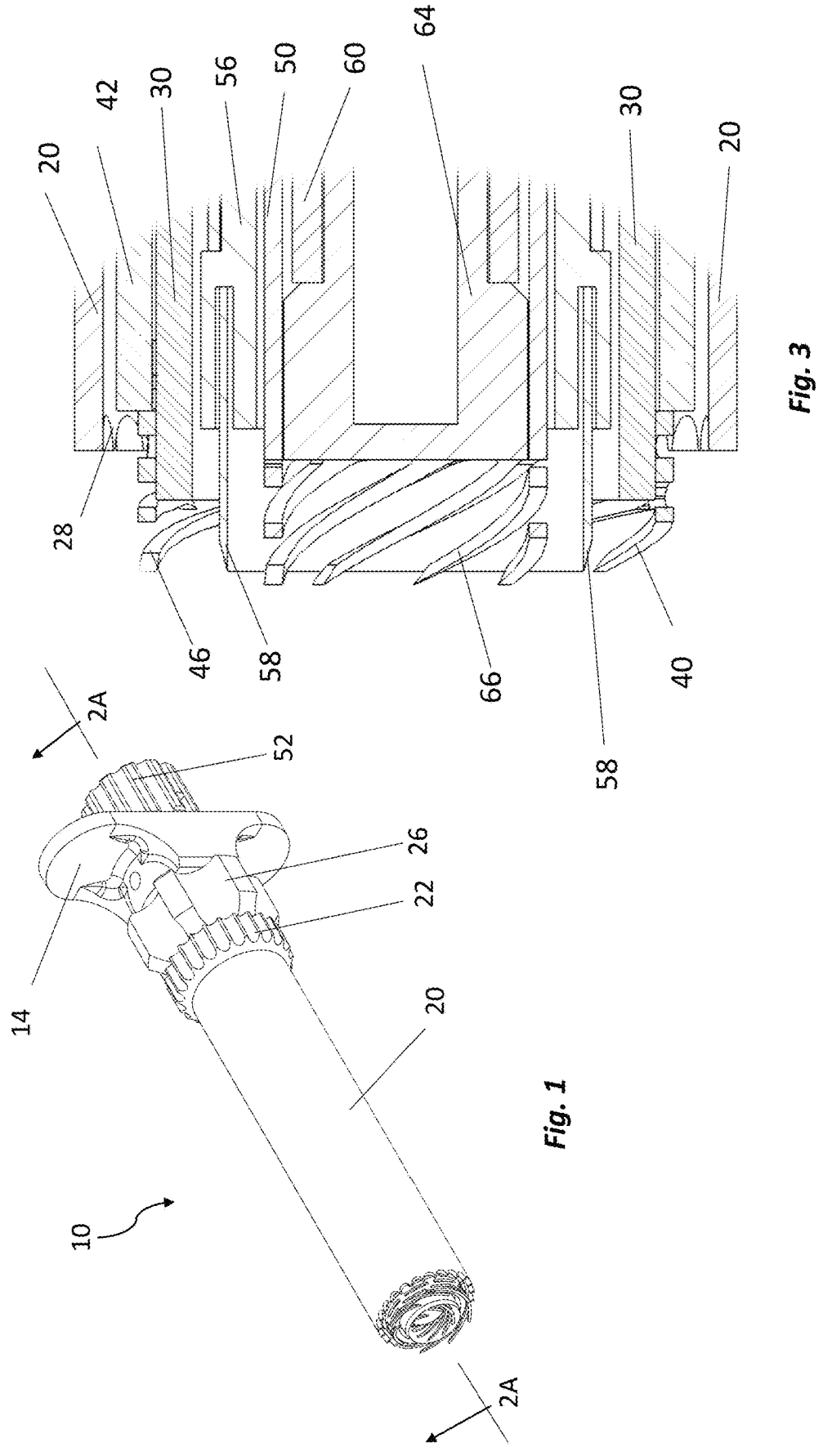
FIG. 1 is a perspective view of an end-to-side connection assembly in accordance with the present disclosure.
FIG. 3 is an enlarged fragmentary view taken along circled area 3 of FIG. 2.

For purposes of clarity, the following terms used in this patent application will have the following meanings:

The terminology used herein is for the purpose of describing example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the order discussed or illustrated, unless specifically identified as an order of performance. It is also to be understood that additional or alternative steps may be employed.

When an element or layer is referred to as being "on," "engaged," "connected," or "coupled" to or with another element, it may be directly on, engaged, connected or coupled to the other element or layer, or intervening elements or layers may be present. In contrast, when an element is referred to as being "directly on," "directly engaged to," "directly connected to," or "directly coupled to" or with another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless dearly indicated by the context. Thus, a first dement, component, region, layer or section discussed below could be termed a second element, component, region, layer or section without departing from the teachings of the example embodiments.

Spatially relative terms, such as "inner," "outer," "beneath," "below," "lower," "above" "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

"Substantially" is intended to mean a quantity, property, or value that is present to a great or significant extent and less than, more than or equal to total. For example, "substantially vertical" may be less than, greater than, or equal to completely vertical.

"About" is intended to mean a quantity, property, or value that is present at ±10%. Throughout this disclosure, the numerical values represent approximate measures or limits to ranges to encompass minor deviations from the given values and embodiments having about the value mentioned as well as those having exactly the value mentioned. Other than in the working examples provided at the end of the detailed description, all numerical values of parameters (e.g., of quantities or conditions) in this specification, including the appended claims, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range, including endpoints given for the ranges.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the recited range, unless otherwise indicated herein, and each separate value is incorporated into the specification as if it were individually recited herein.

References to "embodiment" or "variant", e.g., "one embodiment," "an embodiment," "example embodiment," "various embodiments," etc., may indicate that the embodiment(s) or variant(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment or variant, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The terms "proximal" or "distal" are intended to be relative positional references and are used with reference either to a direction of blood flow relative to a device or device component or with reference to a longitudinal axis of a device or device component. For example, with reference to the graft component, the proximal end of the graft component furthest away from the major vessel or anatomic passageway, whereas the distal end of the graft is the end closest to the major vessel or anatomic passageway.

The term "annular" when used in connection with an element is intended to mean a ring-like structure comprised of either a unitary structure or a discontinuous structure having plural arcuate sections arranged into a ring-like structure.

The term "saddle-shape" when used in connection with an element is intended to mean a generally hyperbolic paraboloid structure.

The term "graft" is intended to refer to any type of polymeric, biological, composite or metal structure.

The term "anatomic passageway" is intended to refer to any anatomical structure having a lumen. Examples of anatomic passageways are blood vessels, the gastrointestinal track, including the esophagus, stomach, small intestine, large intestine, and rectum, or airway passages, such as the trachea and bronchi.

The terms "major vessel" and/or "aorta" as used herein reference specific and non-limiting examples of anatomic passageways. It is intended that the terms "anatomic passageway," "major vessel," and/or "aorta" are used interchangeably and synonymously.

The term "flange" is intended to refer to any type of radially extending projection, including, without limitation, a projection that extends less than or equal to 360 degrees relative to the element that the projection extends from. Further, a flange may have a longitudinal component to its projection orientation relative to the element that the projection extends from.

This detailed description of exemplary embodiments references the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not for purposes of limitation.

Figure 5:
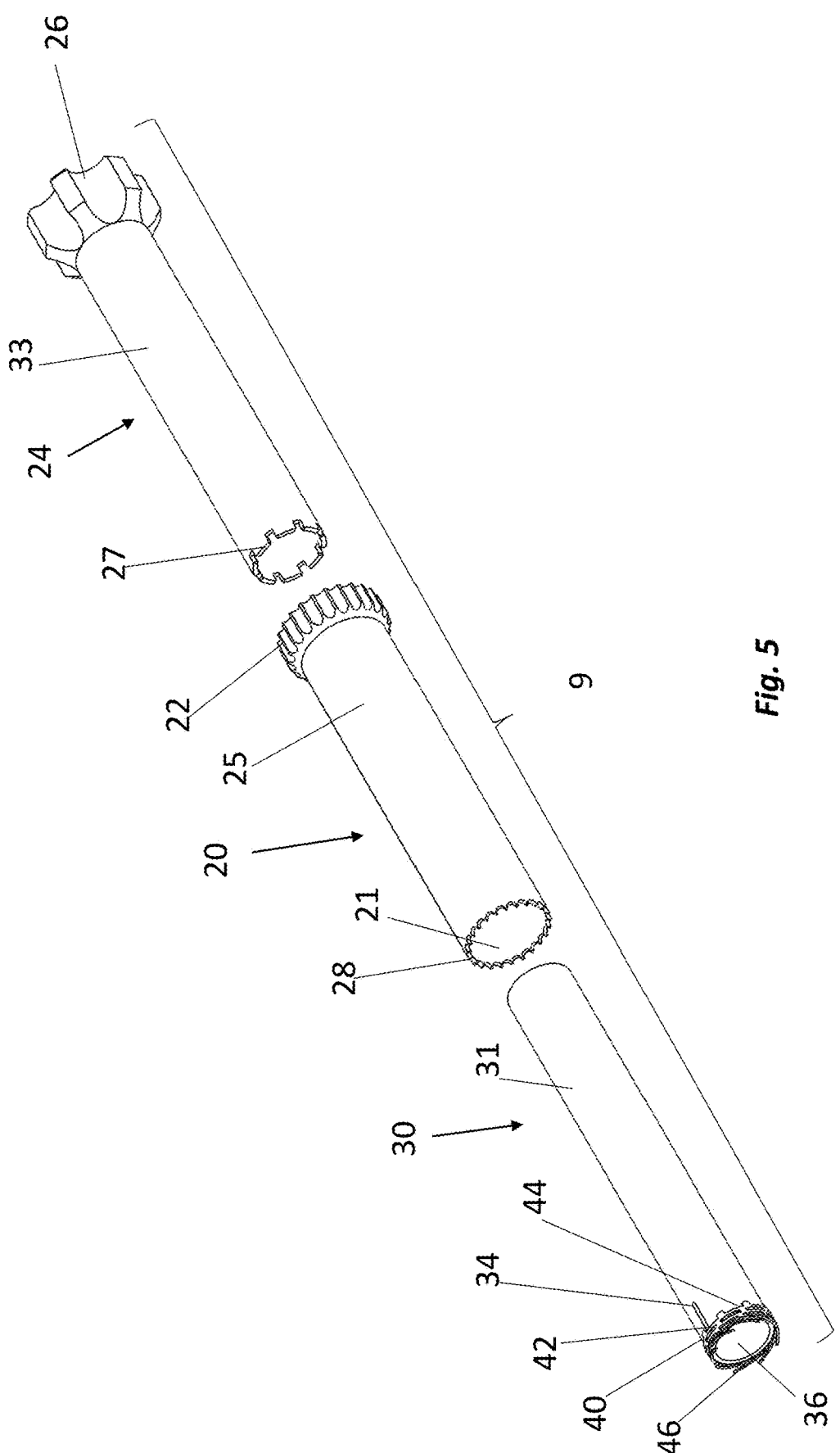
FIG. 5 is a perspective exploded view of a graft delivery component in accordance with the present disclosure.
Figures 6, 7:
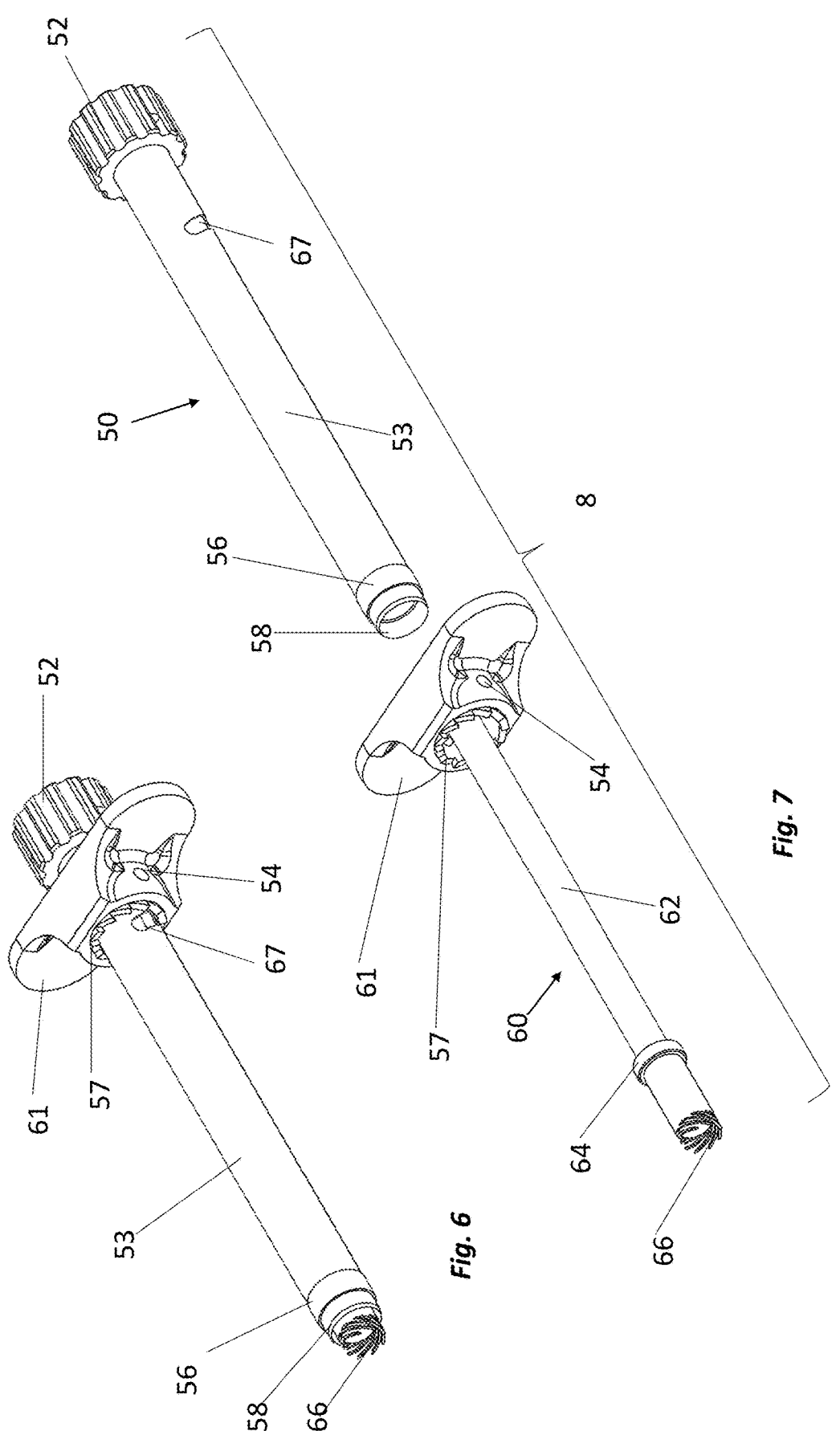
FIG. 6 is a perspective view of an assembled stabilization component and coring component in accordance with the present disclosure.
FIG. 7 is a perspective exploded view of a stabilization component and coring component in accordance with the present disclosure.

The accompanying Figures, in particular, FIGS. 1 to 9D, illustrate various embodiments of the end-to-side connection assembly, starting with assembly 10 (hereinafter "assembly 10"). Assembly 10 includes an axial compression component 20, a graft component 30, an annular ring member 40 having helically oriented tines 46 projecting distally therefrom, an annular ring driver 24, a coring component 8, and a stent component 70. The axial compression component graft component 30, annular ring member 40, and annular ring driver 24 all operably cooperate with one another as the graft delivery system 9, as shown in FIG. 5. The assembly 10 is configured such that the various individual components cooperate with one another and enable the surgeon to create the end-to-side attachment without having to exchange multiple devices or components over guidewires, without the need for a side-biting clamp, complete aortic clamping, and/or without the need to suture any aspect of the end-to-side connection. This results in significant procedural time savings, minimal blood loss, and minimal patient trauma.

The axial compression component 20 includes a tubular housing 25 having a lumen 21 that passes through the tubular housing 25 and opens at proximal and distal ends of the tubular housing. A handle 22 is provided at the proximal end of the tubular housing to allow a surgeon to longitudinally translate the tubular housing 25 and/or rotate the tubular housing 25 about its longitudinal axis. At least one of a plurality of tissue engaging projections 28 are provided at a distal compression section 29 of tubular housing 25. In use, when the tissue engaging projections 28 are brought into contact with anatomic tissue, the area of anatomic tissue circumscribed by the distal end of the distal compression section 29 of tubular housing 25 and the tissue engaging projections 28 will flatten to assist in attaching the graft component 30 to the anatomic tissue.

The graft component 30 includes a tubular graft member 31 having proximal and distal ends thereof. Optionally, an alignment indicia 34 may be provided on the tubular graft member 31, such as proximate to a distal end of the tubular graft member. Alignment indicia 34 may be employed to assist the surgeon in positioning the tubular graft member 31 on the anatomic tissue. As is known in the art, the tubular graft member 31 may be made of biocompatible polymers, such as polyester, e.g., DACRON, polytetrafluoroethylene (PTFE), e.g., expanded polytetrafluoroethylene (ePTFE), polyurethane, autologous biological grafts, allogeneic biological grafts, xenograft biological grafts, biocompatible metals or combinations thereof.

The tubular graft member 31, optionally, may also have, in whole or in part, a graft reinforcement that serves as a support structure for the tubular graft member 31. Further, the tubular graft component may also have a flanged distal section, such as that described in U.S. Pat. No. 6,652,578, which is hereby incorporated by reference in its entirety, teaching a cardiac valve stent having a stent-like support structure with an anchoring flange and a DACRON or expanded polytetrafluoroethylene ("PTFE") graft supported on either or both of a luminal or abluminal surface surfaces or the stent-like support structure. PTFE grafts having an enlarged or flanged skirt for end-to-side anastomosis, and methods of making the same are exemplified by U.S. Pat. Nos. 6,190,590, 6,203,735 and/or 9,445,886, each of which is incorporated by reference.

The annular ring member 40 consists generally of a ring 42 that extends less than or equal 360 degrees and may be a continuous or discontinuous structure. A plurality of tines 46 project distally from the ring 42 and are configured to have a helical orientation oriented relative to a longitudinal axis of the ring 42. As illustrated in FIGS. 10-23, both the ring 42 and the plurality of tines 46 may have a wide degree of variants in geometry, orientation, and construction, which will be described in greater detail below. Generally, however, each annular ring member 40 has the three main components consisting of the ring 42, the plurality of tines 46, and a plurality of driver couplings 44. Other components, such as barbs 128, 129 may be provided on either the tines 46 or the ring 42 or strain relief members 119, may optionally be provided on the annular ring member 40 or between tines 46. The ring 42 also includes at least one of a plurality of driver couplings 44 on a proximal end of the ring 42. The at least one of a plurality of driver couplings 44 interface with at least one of a plurality of driver engagements 27 on the driver component 24, which will be described in greater detail below.

Optionally, the plurality of tines 46, the ring 42, or the strain relief members 119 may have a coating or covering of a procoagulation pharmacologically active agent that promotes coagulation. Examples of procoagulation agents include fibrin adhesives, thrombin, adenosine diphosphate (ADP), thromboxane A2 (TXA2), 5-hydroxytryptamine (serotonin), epinephrine, vasopressin, fibrinogen, immune complexes, plasmin, and/or platelet-activating factor.

The plurality of tines 46 extend distally from the ring 42 and are helically oriented relative to a circumferential axis of the ring 42. Each of the plurality of tines 46 have a taper along their longitudinal axis to allow a distal end of each tine 46 to penetrate and embed into the anatomical tissue. The plurality of tines 46 may have a transverse cross-sectional profile that is configured to either aid in cutting and/or penetrating anatomic tissue or is configured to aid in compression and/or sealing of the anatomic tissue. In the case where the transverse cross-sectional profile of a tine 46 is configured to assist in cutting and/or penetrating anatomic tissue, it is advantageous that the tine have sharp edges such as that with a polygonal transverse cross-section to the tines 46, e.g., triangular, quadrilateral, pentagonal, etc. Alternatively, where the transverse cross-sectional profile of a tine 46 is configured to assist in compression and/or sealing of the anatomic tissue, a more rounded or curvilinear transverse profile to the tines 46 will be desirable, e.g., round, oval, elliptical, etc. It is to be appreciated that an individual tine 46 may have different transverse cross-sectional profiles along a length of the individual tine 46, e.g., may be polygonal at a distal aspect of the tine 46 and rounded or curvilinear at a proximal aspect of the tine 46. Additionally, some of the plurality of tines 46 may have a first transverse cross-sectional profile and others of the plurality of tines 46 may have a second, different transverse cross-sectional profile.

Each of the plurality of tines 46 are generally elongated, have a curvature about an arc that each tine 46 subtends about the circumferential axis of the ring 42. Further, at least some of the plurality of tines 46 may, optionally, be configured to have a curvature along the longitudinal axis of the ring 41, e.g., a proximal and distal oriented curvature, along a length of the tine 46. Finally, at least some of the plurality of tines 46 may have a barb (See, e.g., element 128, FIG. 12; element 218, FIG. 21; element 221, FIG. 22; element 238, FIG. 23) projecting from a portion of the tine 46, wherein the barb projects in an opposite orientation from the associated tine 46. The barb associated with at least some of the plurality of tines 46 will also penetrate and embed into the anatomic tissue as the plurality of tines 46 penetrate and embed into the anatomic tissue. Because of its orientation, however, the barb assists in resisting or preventing counter rotation of the annular ring member 40 and potential disengagement or dislodging of the annular ring member 40 from the anatomic tissue.

The ring 42 is affixed to a distal end of the tubular graft member 31. Such affixation may be achieved by a number of mechanisms, including, without limitation, using a biocompatible adhesive, such as a ultraviolet curable adhesive, providing a polymer cover and covering the ring 42 with the polymer cover and shrinking the polymer cover over the ring 42 or thermally reflowing the polymer cover and the tubular graft member 31 (where it is a polymer suitable for thermal reflow processing) to encapsulate the ring 42 within the reflowed polymer covering and tubular graft member 31, using a biocompatible adhesive to join a polymer covering with the ring 42 and the tubular graft member 31, or other similar mechanisms for affixing the ring 42 to the tubular graft member 31.

Figure 8:
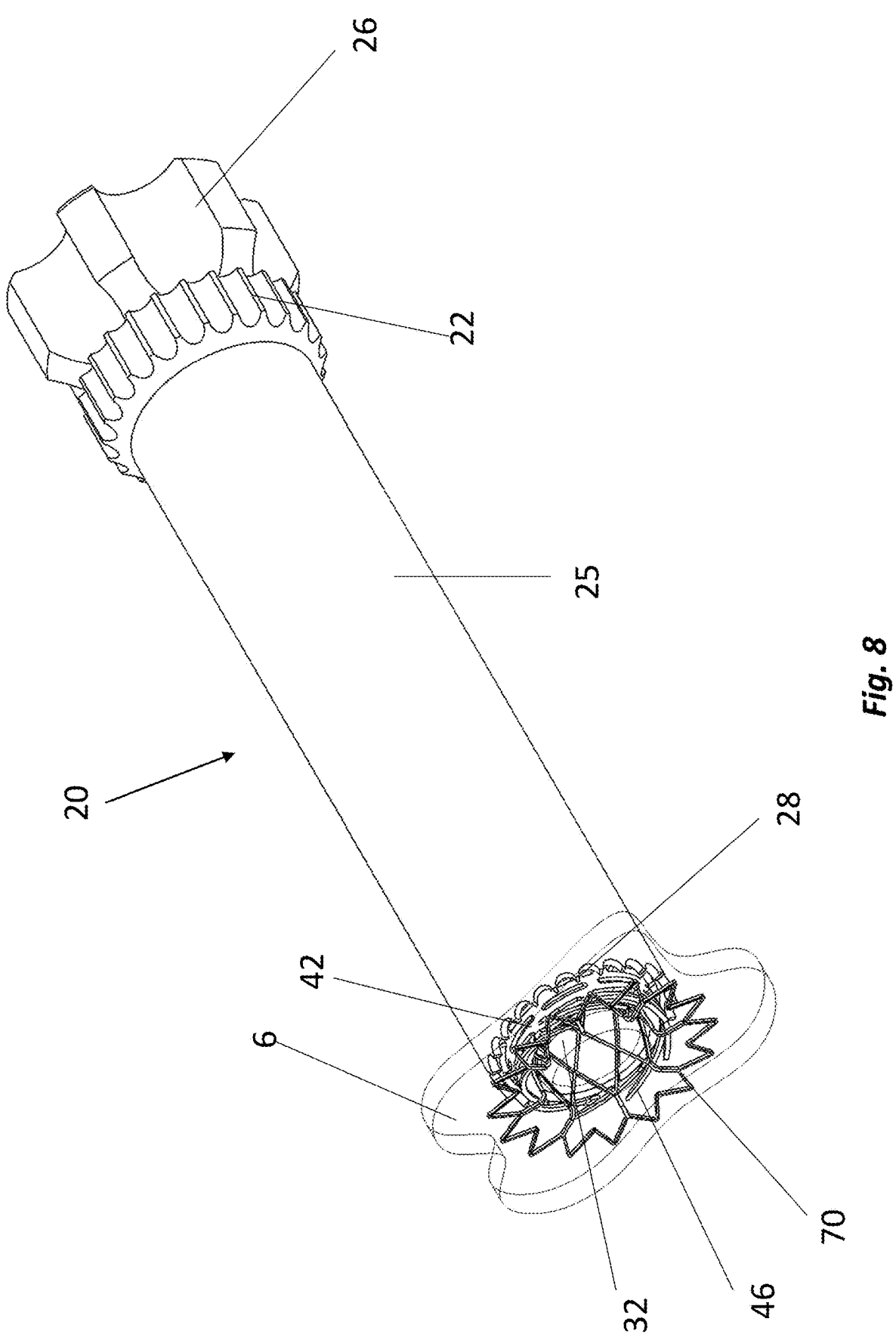
FIG. 8 is a perspective view of an assembled graft delivery system and stent component illustrating its delivery and attachment in an end-to-side connection with anatomical tissue.
Figures 9A, 9B:
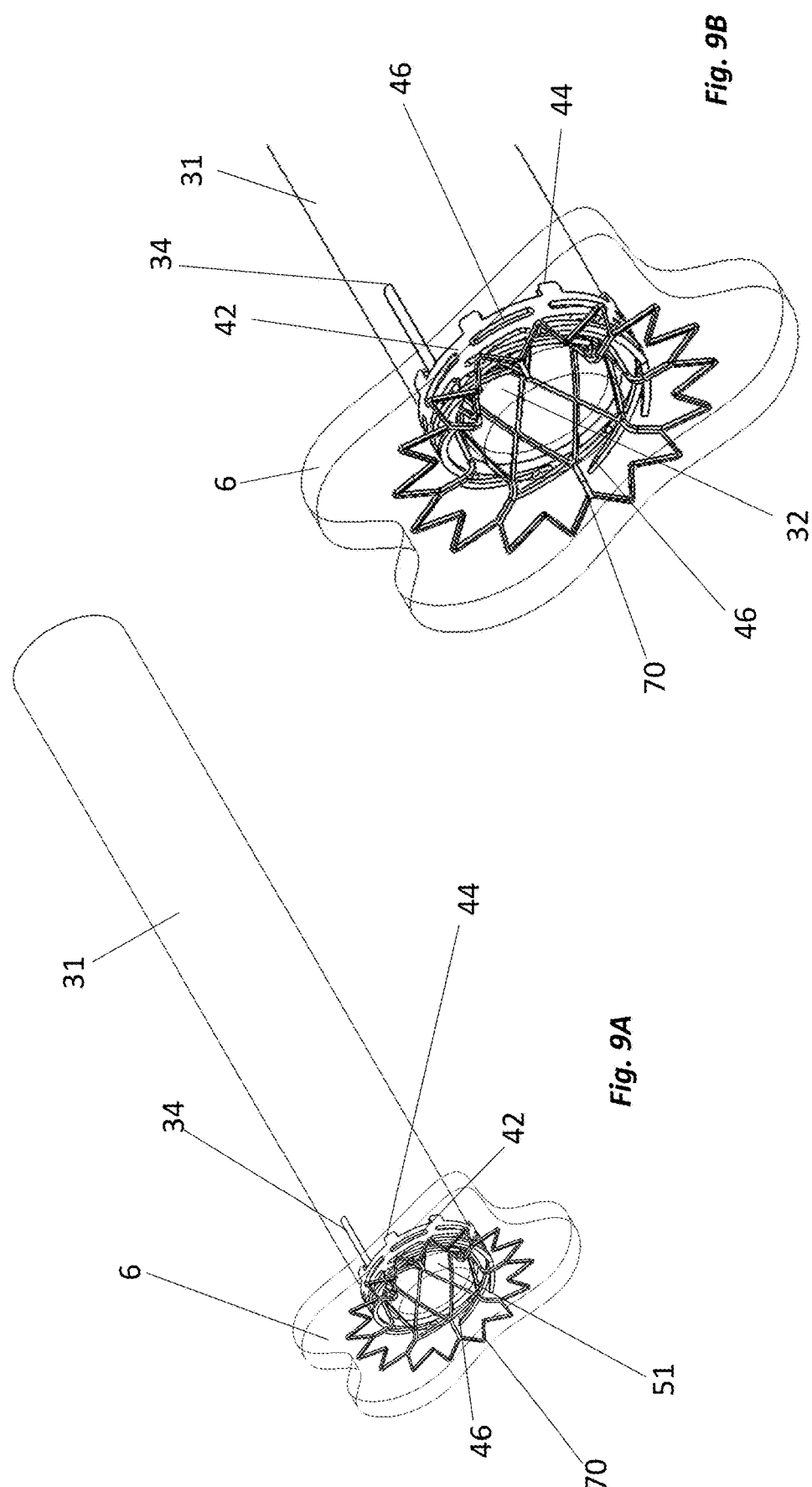
FIG. 9A is a perspective view of an affixation component, a graft, and a stent component illustrating attachment in an end-to-side connection with anatomical tissue.
FIG. 9B is an enlarged perspective view of the stent component, a graft, and a stent component of the end-to-side connection with anatomical tissue in accordance with the present disclosure.
Figures 9C, 9D:
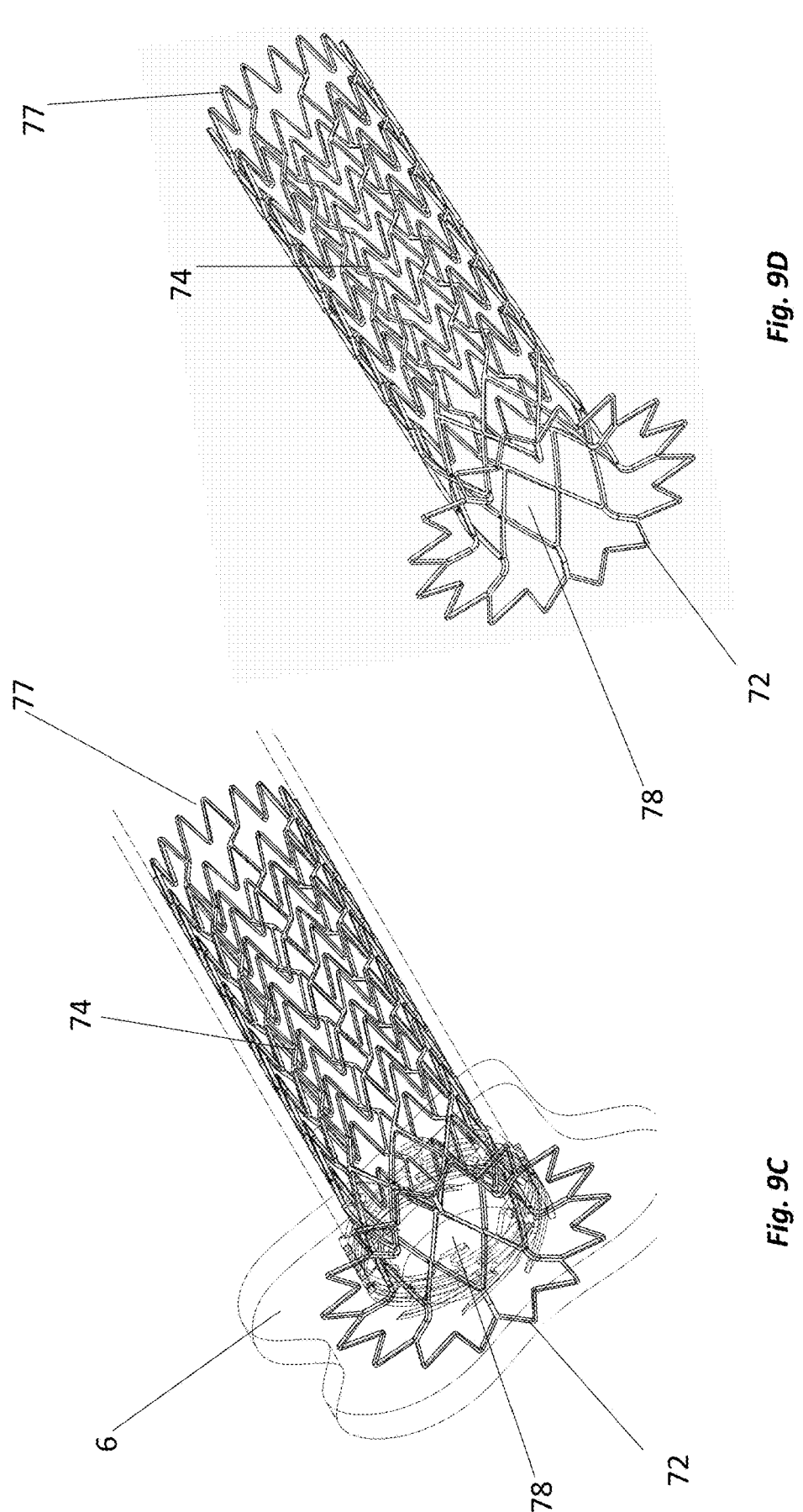
FIG. 9C is a perspective view of the stent component deployed within the graft component with the flanged portion of the stent component abutting the anatomic tissue.
FIG. 9D is a perspective view of the stent component in its fully deployed expanded state.
Figure 10:
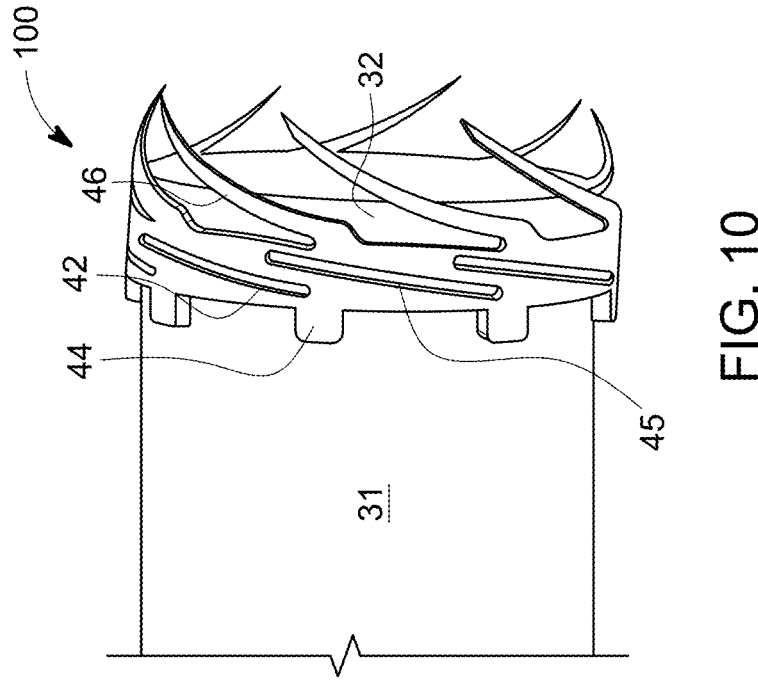
FIG. 10 is a photograph illustrating a variant of an attachment device coupled to a distal end of a graft in accordance with the present disclosure.

To assist in imparting a fluid tight seal between the ring 42, the tubular graft member, and the anatomical tissue 6, as illustrated in FIGS. 8 to 10, a distal end 32 of the tubular graft member 31 may project distally from the ring 42. In this configuration, the distal end 32 of the tubular graft member 31 is axially compressed against the anatomic tissue and may be radially compressed, by stent 70, against the opening created by coring the anatomic tissue. The extent by which the distal end 32 of the tubular graft projects distally from the ring 42 may be configured to correspond to the wall thickness of the anatomic tissue. Typically, however, the distal end 32 of the tubular graft 31 will preferably project between about 0.5 mm to about 3 mm from a distal end of the ring 42.

Turning to FIGS. 8 to 9D, the stent component 70 is shown deployed with the distal circumferential flange 72 of the stent component 70 deployed on a first surface of anatomic tissue 6 and a proximal stent section 74 deployed within the tubular graft member 31 of the graft component 30. The stent component 70 is deployed after the annular ring member 40 is affixed to the anatomical tissue 6. Affixation of the annular ring member 40, the tubular graft member 31, and the stent component 70 to the anatomical tissue 6 is illustrated in FIGS. 9A to 9C.

Both the circumferential flange portion 72 and the proximal stent section 74 of the stent component 70 may be configured with structural members defining the walls of the stent component 70 as is conventional with any of the large number of conventional intraluminal stents, with the proviso that a distal end of the proximal stent section 74 is configured to be contiguous with the distal circumferential flange section 72. As is well known in the stent art, most stents have proximal and distal openings of a lumen defined by the structural members of the stent component that allows for fluid flow communication into and through the proximal and distal openings and the lumen of the stent component 70.

Optionally, the stent component 70 may be integrated, in whole or in part, into the tubular graft member 31, such as by embedding into or encapsulated by the tubular graft member 31. For example, the proximal stent section 74 may be integrated into a distal portion of the tubular graft member 31, with the distal circumferential flange section 72 left without covering. Alternatively, the distal circumferential flange section 72 may have partial or complete covering that expands by unfolding or deformation during deployment of the distal circumferential flange section 72. Further, both the proximal stent section 74 and the distal circumferential flange section 72 may have partial or complete coverings that expand by unfolding or deformation during deployment of the stent component 70.

Where the stent component 70 is integrated with the tubular graft member 31, the tubular graft member 31 may be positioned on the luminal and/or abluminal wall surfaces of the proximal section 74 of the stent component 70. The tubular graft member 31 may be secured to either the proximal section 74 on either the luminal or abluminal wall surface thereof, or where a tubular graft member 31 is secured to both the luminal and abluminal wall surfaces of the proximal portion 74 of the stent component 70, the luminal and abluminal tubular graft members 31 may be affixed to each other through interstices of the stent component 70. An example of an integrated graft with a stent is found at U.S. Pat. No. 5,749,880 ("the '880 Patent") which discloses an ePTFE covering on both the luminal and abluminal surfaces of a stent and encapsulating the stent through interstices in the stent. The '880 Patent is hereby incorporated by reference in its entirety as if fully set forth herein.

When the stent component 70 is deployed, the distal circumferential flange section 72 nests against a first surface of the anatomic tissue 6, e.g., a luminal wall surface of an anatomic passageway. Further, when fully deployed, the distal circumferential flange section 72 also bears against the first surface of the anatomic tissue and applies an axially compressive force against the anatomic tissue and the annular ring member 40 that is vectored toward the tubular graft member 31 and the annular ring member 40. Moreover, when fully deployed, the proximal stent section 74 exerts a radially expansive force against both the lumen of the tubular graft member 31 and an inner circumference of the annular ring member 40. The combination of the axially compressive force exerted by the distal circumferential flange section 72 and the radially expansive force exerted by the proximal stent section 74 aid in maintaining and retaining the position of the stent component 70, the tubular graft member 31 and the annular ring member 40 relative to the anatomic tissue 6. This mechanism seals the connection between the annular ring member 40, the tubular graft member 31, and the anatomic tissue 6 and prevents fluid leakage.

Optionally, a plurality of projecting barbs may be provided on at least some of the structural members of the stent component 70 that are configured to embed either in the anatomic tissue 6 and/or the luminal wall of the tubular graft member 31, to further assist in retaining the deployed position of the stent component 70.

The distal circumferential flange section 72 may, optionally, be configured to have a shape that conforms to the curvature of the first wall surface of the anatomic tissue, e.g., a luminal wall surface of an anatomic passageway. To accomplish this, the distal circumferential flange section 72 may be programmed to a substantially saddle-shape, in the case of a shape memory or superelastic material or may be set to a substantially saddle-shape by a balloon or anvil introduced against the first wall surface of the anatomic tissue. In either case, the saddle-shape of the distal circumferential flange section 72 serves to form a close abutment and approximation between the circumferential flange section 72 and the first wall surface of the anatomic tissue, e.g., the abluminal wall an anatomic passageway.

It will be appreciated by those skilled in the art, that access through the anatomic tissue 6 must be established in order to permit fluid flow through the tubular graft member 31 and the stent component 70. For example, where the end-to-side connection is made to a major blood vessel 6, an opening must be made to accommodate blood flow from the tubular graft member 31 and into the lumen of the major blood vessel 6. In the present disclosure, such access is made by providing the coring component 8. Coring component 8 consists generally of a stabilization member 60 and a coring member 50. Stabilization member 60 and coring member are configured to cooperate with one another in that the coring member 50 is configured to longitudinally translate with respect to the stabilization member 60. Stabilization member 60 is configured to be removably coupled to the anatomic tissue 6 and coring member 50 longitudinally translates with respect to stabilization member 60 to cut a tissue core around a distal end of the stabilization member 60, with the cut tissue core being retained at a distal end of the stabilization member 60 and removable therewith.

Stabilization member 60 consists of an elongate stabilization member 62 having a stabilization handle 61 at a proximal end thereof and at least one of a plurality of stabilization tines 66 at a distal end thereof. The plurality of stabilization tines 66 may have a helical orientation relative to the longitudinal axis of the stabilization member 60, in either a clockwise or counterclockwise direction or may be oriented substantially parallel to the longitudinal axis of the stabilization member 60. The plurality of stabilization tines 66 may also include at least one of a plurality of barbs projecting laterally from one or more of the plurality of stabilization tines 66 to further secure a cored tissue plug 7 on the plurality of stabilization tines 66. A stabilization spacer 64 may optionally be provided about an outer circumference of the elongate stabilization member 62 to maintain concentric alignment between the stabilization member 60 and the coring member 50. Optionally a plurality of engagements 57 may be provided in association with stabilization handle 61 to permit operable engagement with and co-manipulation of the stabilization handle 61 and driver handle 26 of the driver component 24, described above. Optionally, the stabilization handle 61 may have a flush port opening 54 operably associated therewith.

Coring member 50 consists of an elongate coring member 53 having a coring handle 52 at a proximal end of the elongate coring member 53 and at least one coring knife 58 at a distal end of the elongate coring member 53. The at least one coring knife 58 is affixed to the distal end of the elongate coring member 53 by any number of mechanisms, such as, for example, a knife retaining member 56 that fixedly couples the at least one coring knife 58 to the elongate coring member 53. Where the elongate coring member 53 is a tubular structure, an optional guide slot 67 may be provided in a side wall of the elongate coring member 53 to facilitate positioning of the elongate coring member 53 relative to the elongate stabilization member 62.

Figure 2A:
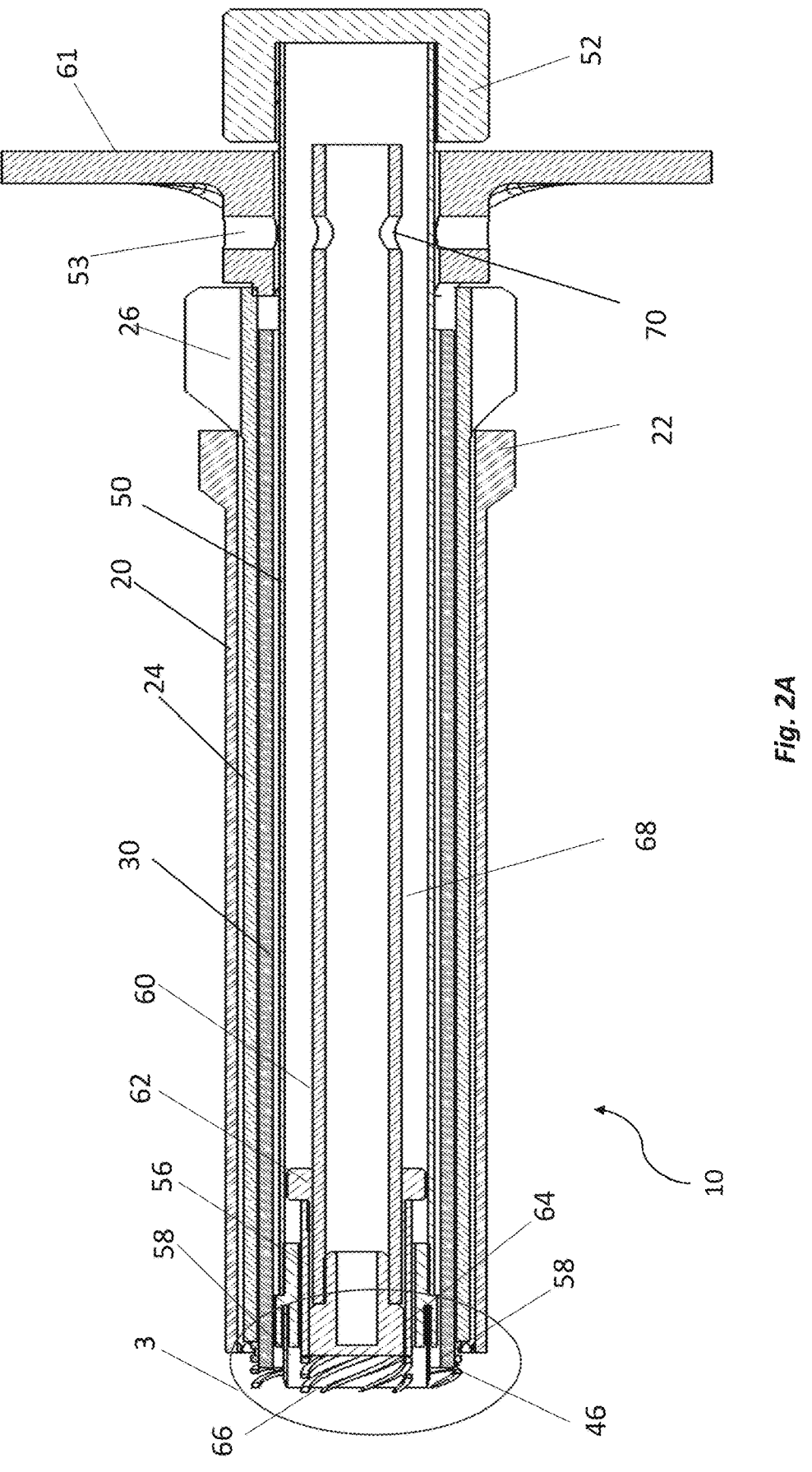
FIG. 2A a cross-sectional view of the end-to-side connection assembly taken along line 2A-2A of FIG. 1.
Figure 2B:
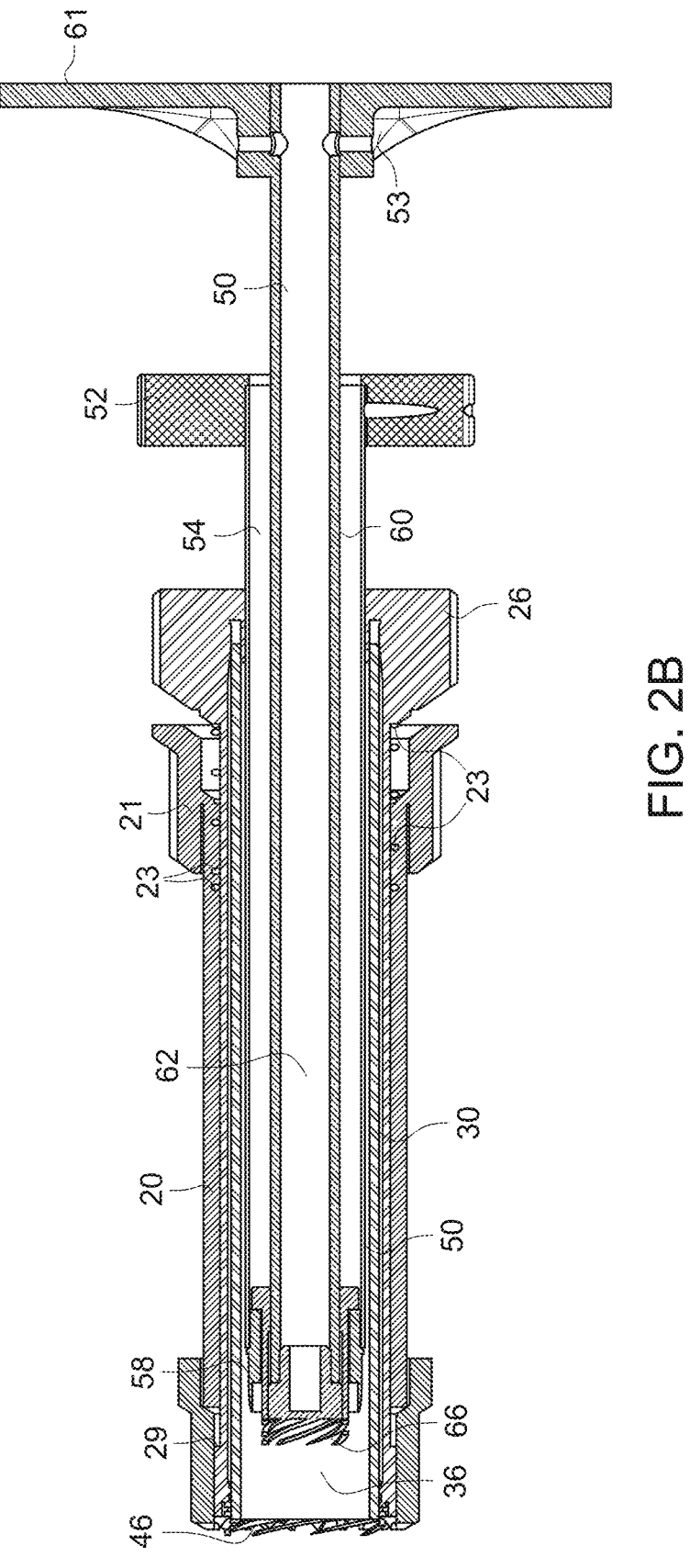
FIG. 2B is a cross-sectional view of an alternative end-to-side connection assembly in accordance with the present disclosure.
Figure 2C:
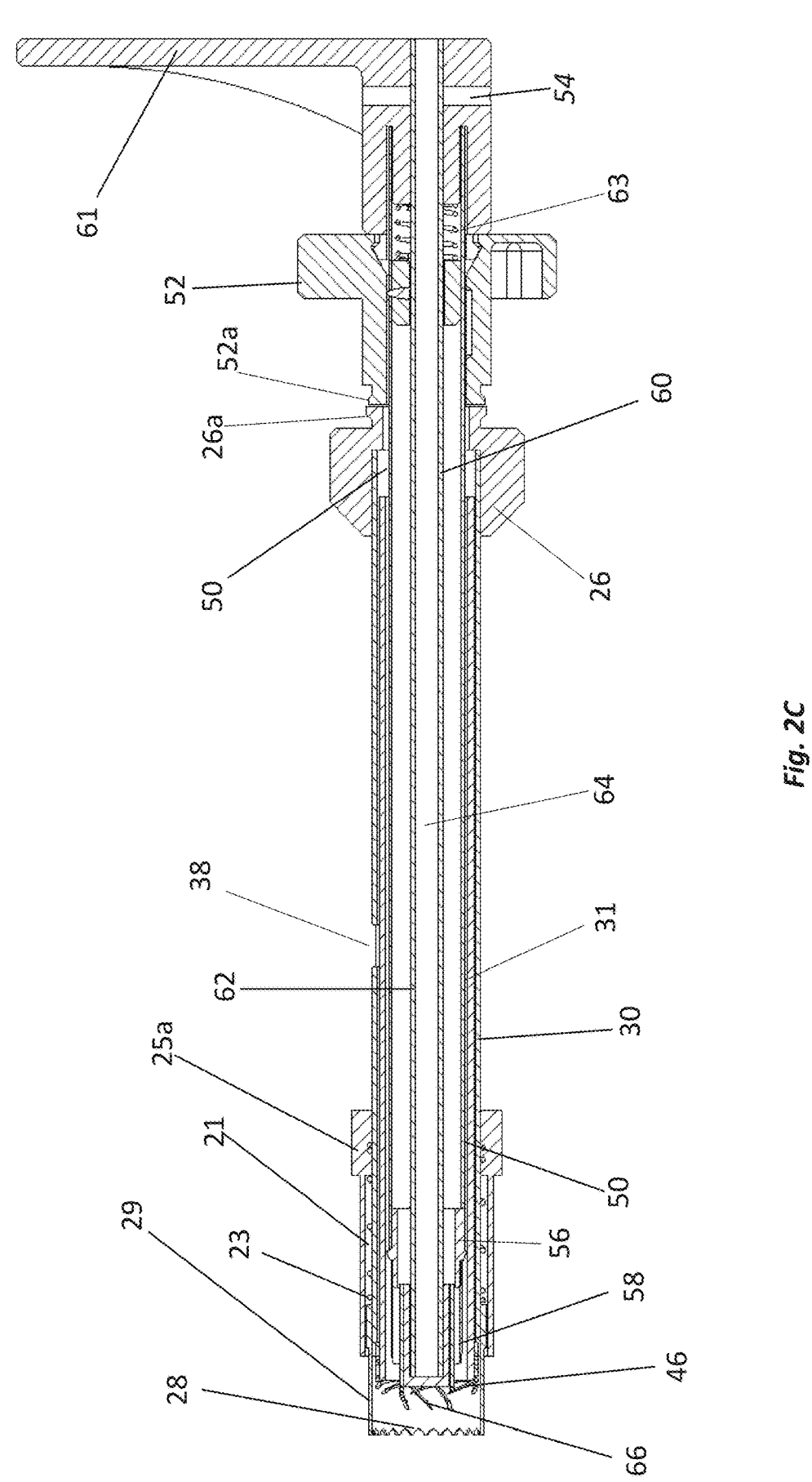
FIG. 2C is a cross-sectional view of another alternative end-to-side connection assembly in accordance with the present disclosure.
Figure 4:
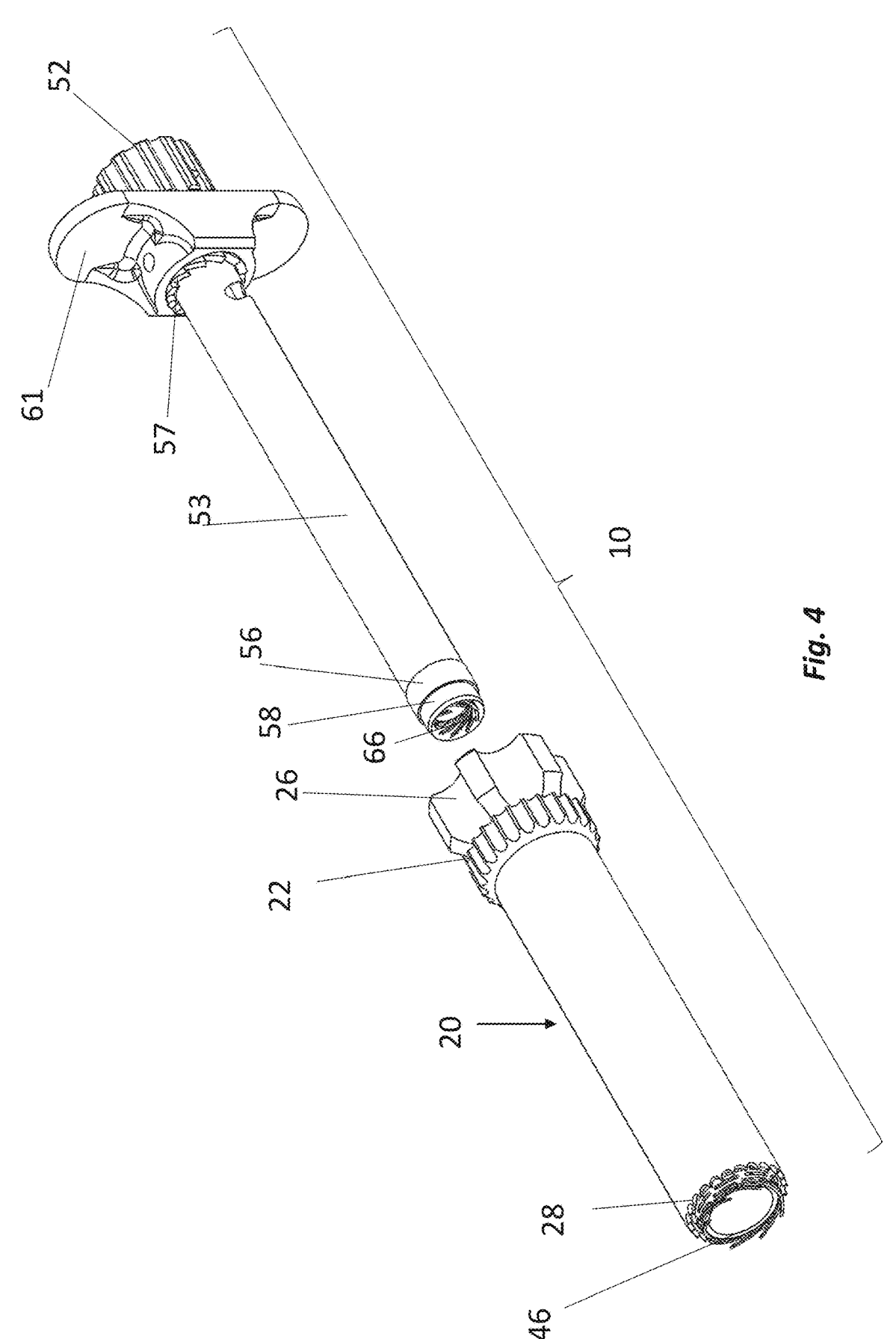
FIG. 4 is a perspective exploded view of a graft delivery component and a coring component in accordance with the present disclosure.

As shown in FIGS. 2A-2C, when assembled into assembly 10, the stabilization member 60 is positioned centrally along a longitudinal axis of assembly 10, the coring member is concentrically positioned about the stabilization member 60 with a space 68 therebetween. The graft component 30 is then positioned concentrically about the coring member 50 with the driver component 24 concentrically positioned about the graft component 30. The driver engagements 27 of the driver component 24 operably engage with the tine ring driver couplings 44 on the tine ring 42 coupled to the tubular graft member 31 of the graft component 30. The axial compression component 20 is then concentrically positioned about the graft component 30. This arrangement of assembly 10 permits longitudinal translation of the axial compression component 20 independent of the driver component 24 to allow the axial compression component 20 to engage with the anatomic tissue 6 and flatten tissue area to which the tine ring 42 will be joined. Once the axial compression component 20 is engaged with and flattens the anatomic tissue 6, the driver component 24 engaged with the tine ring 42 is longitudinally translated independently of the axial compression component 20 and/or the coring member 50 and the tine ring 42 is engaged with the anatomic tissue 6 by rotating the driver component 24 and the tine ring 42 which embeds the plurality of tines 40 into the anatomic tissue and axially compresses the tubular graft member 31 against the anatomic tissue 6.

As shown in FIG. 2B, an axial compression spring 23 may, optionally, be provided that interacts with the axial compression component 20 and the graft component 30. Axial compression spring 23 limits travel of the axial compression component 20 relative to the graft component. Axial compression spring 23 is also provided in the alternative embodiment of assembly 10 shown in FIG. 2C, but when compared to the embodiment illustrated in FIG. 2B, the axial compression spring 23 interacts between a proximal portion 25a of the axial compression housing 25 and the distal compression member 29 to limit travel of the distal compression member 29 relative to the proximal portion 25a of the axial compression housing 25. Further, as shown in FIG. 2C, a spring 63 is provided that surrounds the elongate stabilization member 62 and bears against the stabilization handle 61 and the coring handle 52 to limit relative travel between the stabilization component 60 and the coring component 50 as well as apply an axial force to the coring knife 58. Optionally, coring handle 52 may have a coring handle coupling 52a and driver handle 26 may have a driver handle coupling 26a. An engagement space 55 is provided between coring handle coupling 52a and driver handle coupling 26a that is expansible by longitudinally translating the coring handle 52 and compressing spring 63 and then placing a retaining member, such as a clip (not shown) into he opened engagement space 55 to maintain the opened engagement space 55 until tissue coring is required. Alternatively, the driver handle coupling 26a and the coring handle coupling 52a may be removably coupled to each other by removable engagement therebetween spanning the engagement space 55. Such removable engagement may be achieved by a mechanical coupling between the coring handle coupling 52a and the driver handle coupling 26a, such as, for example, a friction fit or an external clip that engages both elements.

Figure 24:
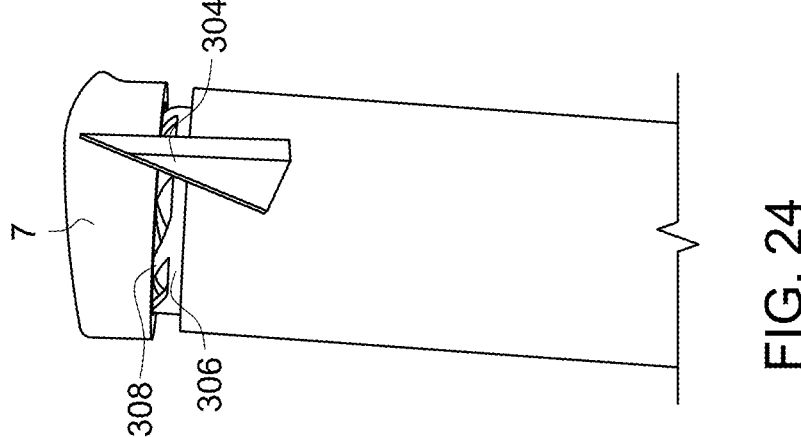
FIG. 24 is a photograph illustrating the stabilization component and the coring component with a test aortic core attached thereto in accordance with the present disclosure.
Figures 26A, 26B, 26C, 26D, 26E, 26F, 26G:
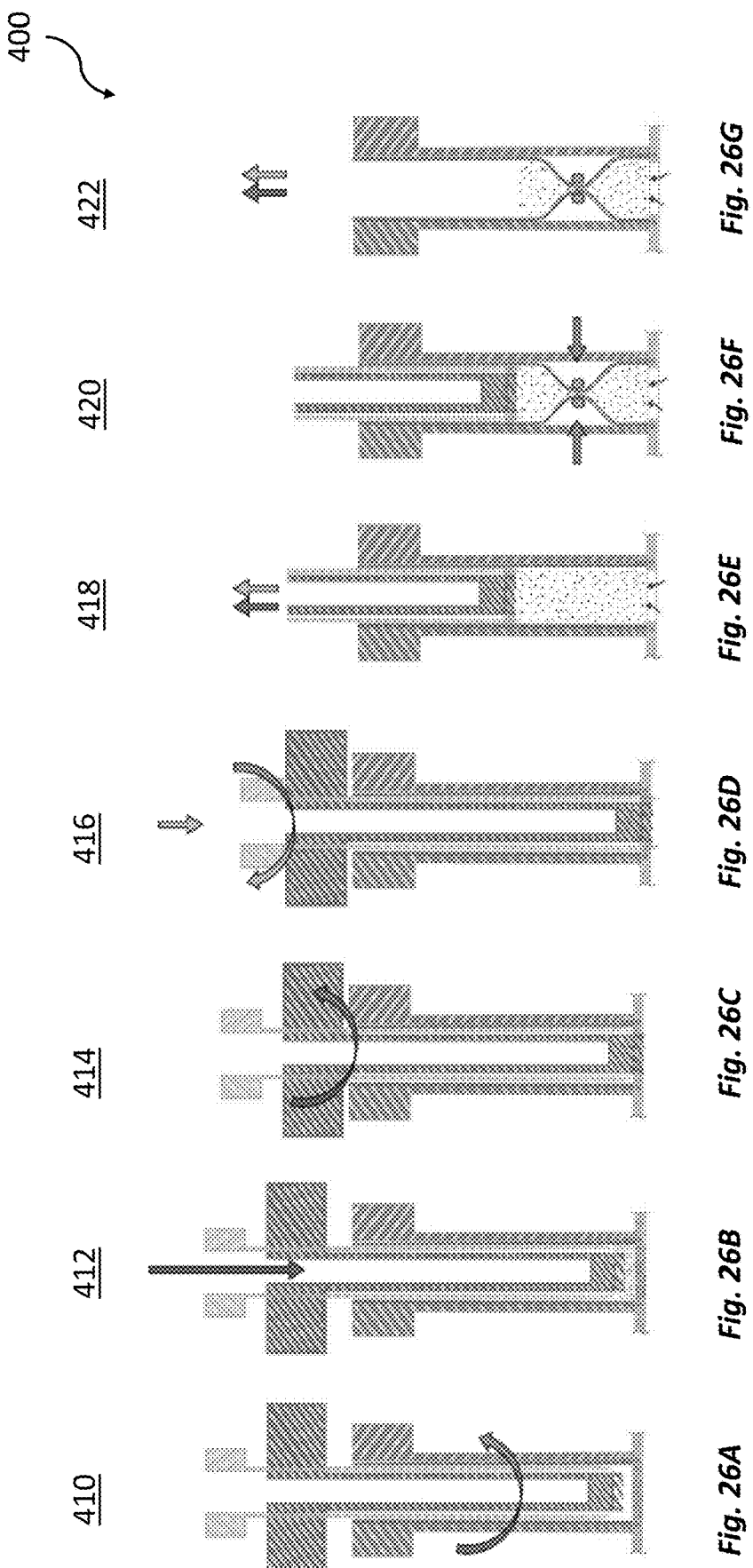
FIGS. 26A-26G are sequential diagrammatic views illustrating a method for delivering the graft component, coring anatomic tissue, and hemostatically withdrawing the tissue core in accordance with the present invention.
Figures 27A, 27B, 27C, 27D, 27E, 27F, 27G, 27H:
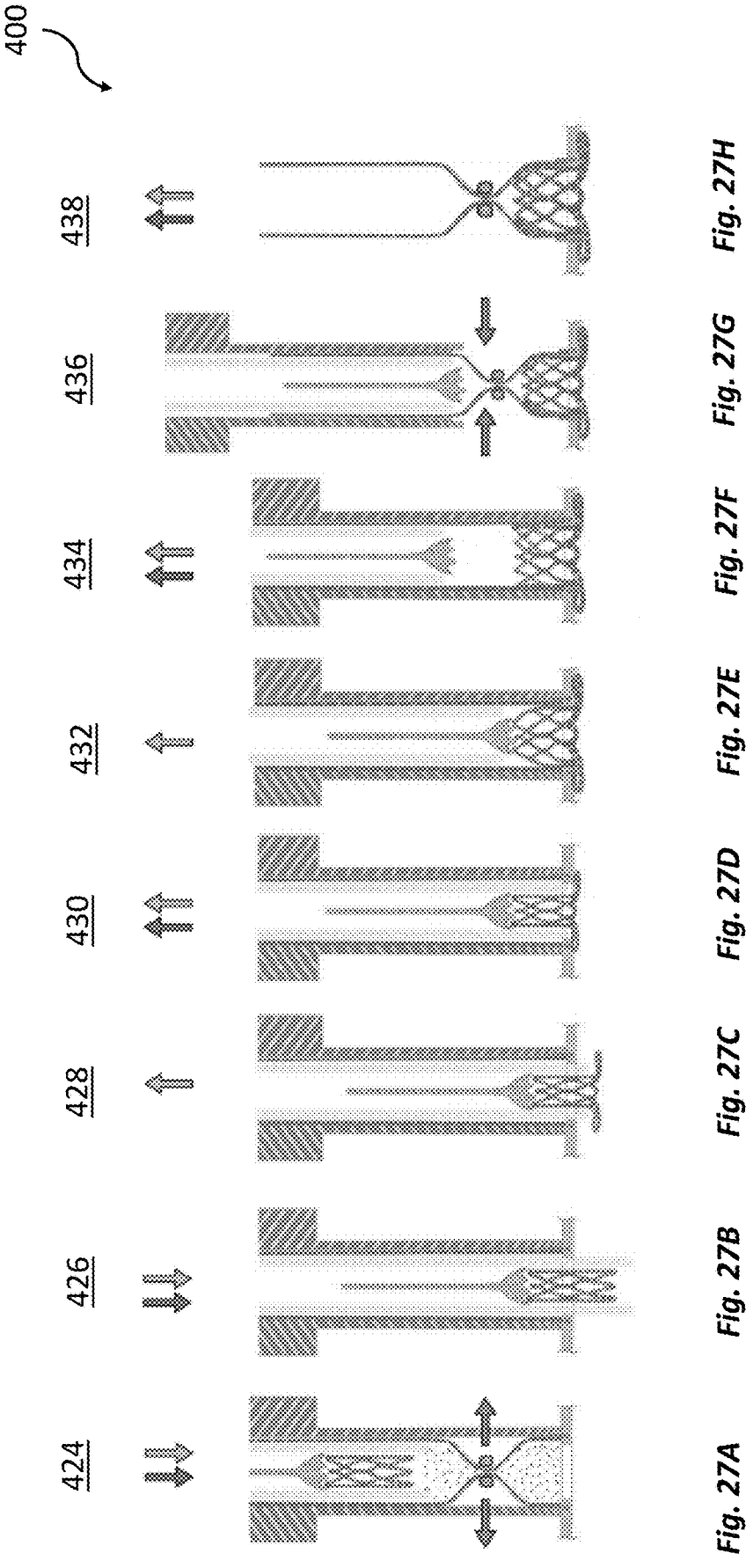
FIGS. 27A to 27H are sequential diagrammatic views illustrating a method for delivering the stent component and withdrawing the graft delivery system in accordance with the present invention.

Once the tine ring 42 and tubular graft member 31 are coupled to the anatomic tissue 6, the stabilization member 60 is then longitudinally translated and advanced such that the plurality of stabilization tines 66 is abutting with the anatomic tissue. Thereafter, the stabilization handle 61 is manipulated, such as by rotating, to drive the stabilization tines 66 into the anatomic tissue 6. The portion of the anatomic tissue 6 that is now coupled to the stabilization tines 66 will become a tissue core plug 7, as shown in FIG. 24. Once the stabilization tines 66 are coupled to the anatomic tissue 6, the coring member 50 is longitudinally translated and the coring knife 58 is advanced into contact with the anatomic tissue. Manipulation, such as by rotation of the coring knife 58, in a diametrically offset relationship from the stabilization tines 66 cuts a tissue core plug 7. Once a coring cut is made in the anatomic tissue 6, the tissue core plug 7 is detached from the remainder of the anatomic tissue 6 and retained on the stabilization tines 66. The entire coring assembly 8 is then partially withdrawn within the graft lumen 36 of the tubular graft member 31. The graft the lumen 36 of tubular graft member 31 is occluded to maintain hemostasis, such as by clamping the tubular graft member 31, prior to complete removal of the entire coring assembly 8 and the tissue core plug 7 from assembly 10.

Turning to FIG. 10, a variant 100 of the annular ring member coupled to the tubular graft member 31 is shown. Annular ring member 100 consists generally of tine ring 42, at least one of a plurality of tines 46 projecting distally from the tine ring 42, at least one of a plurality of tine ring driver couplings 44 on a proximal end of the tine ring 42, and at least one of a plurality of tine ring apertures 45 passing through a wall of the tine ring 42. The at least one of a plurality of tines 40 may be helically oriented relative to a circumferential axis of the tine ring 42. Each of the at least one of a plurality of tines 40 may be tapered along the length of each tine such that a most distal aspect of each of the tines 40 tapers to a point to assist in tissue penetration. Each of the at least one of a plurality of tine ring driver couplings 44 may consist either of projections from a proximal aspect of the tine ring 42, detents in a proximal aspect of tine ring 42, or such other structures that are configured to positively and releasably engage with driver engagements 27 on the driver component 24. The at least one of a plurality of tine ring apertures 45 passing through the wall of the tine ring 42 may be circumferentially positioned about a circumferential axis of the tine ring 42 and configured to allow a biocompatible adhesive, polymer, or other means for joining the tine ring 42 to the tubular graft member 31 to pass through each of the tine ring apertures 45 to join the tine ring 42 to the tubular graft member 31. Finally, as depicted in FIG. 10, the distal end 32 of tubular graft member 31 extends distally from the distal end of the tine ring 42. This extended distal end 32 of the tubular graft member 31 permits axial compression of the distal end 32 when the tines 46 are embedded into anatomic tissue 6 and assist in fluidly sealing the connection between the tubular graft member 31 and the anatomic tissue 6. As noted above, it is postulated based upon experimental testing that the distal end 32 of the tubular graft member 31 may extend distally from the tine ring 42 between about 0.5 mm to about 3.0 mm to enhance the fluid sealing effect resulting from axial compression of the distal end 32 against the anatomic tissue 6 when the tines 46 are embedded into the anatomic tissue 6.

Figure 11:
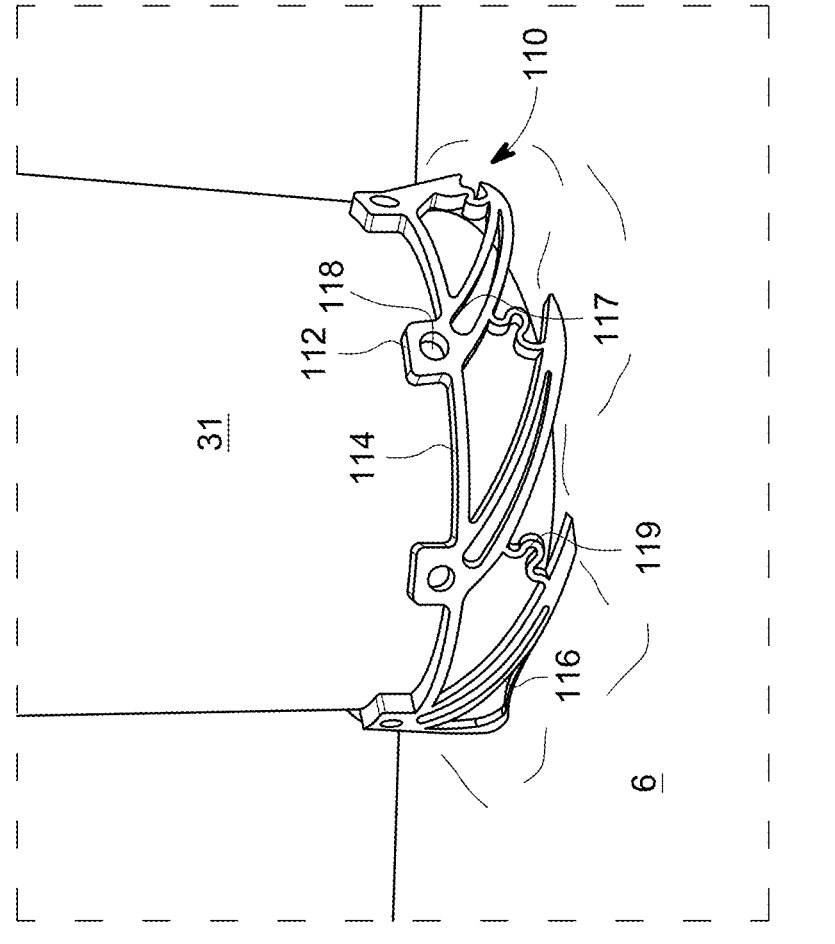
FIG. 11 is a photograph illustrating a variant of an attachment device coupled to a distal of a graft and joined to a pressurized test aorta in accordance with the present disclosure.

FIG. 11 depicts a variant 110 of the annular ring member coupled to a tubular graft member 31 showing the tines 116 embedded into a synthetic experimental anatomic tissue 6 that was pressurized to physiological pressure found in a human aorta. Annular ring member variant 110 consists of a tine ring 114, a plurality of tines 116 projecting from a distal aspect of the tine ring 114, and a plurality of tine driver couplings 112 positioned at a proximal aspect of the tine ring 114. In annular ring member variant 110, the tine rings 116 are helically oriented about a circumferential aspect of the tine ring 114. Each of the tines 116 may, optionally, have a tine aperture 117 passing through the tine 116. Where provided, the tine aperture 117 may be elongated and serve to modulate the elasticity of each tine 116 with which the tine aperture is associated. Alternatively, where provided, the tine aperture 117 may serve as an additional coupling point for joining the annular ring member variant 110 to the tubular graft component 31. Annular ring member variant 110 also includes a joining aperture 118 passing laterally through at least some of the plurality of tine driver couplings 112. The joining apertures 118 may also serve as coupling points for joining the annular ring variant 110 to the tubular graft component 31. Finally, tine strain relief members 119 may optionally be provided that interconnect circumferentially adjacent tines 116. Tine strain relief members 119 will allow circumferentially adjacent tines 116 an order of flexion relative to one another as well as stabilize the tines 116 in a circumferential curvature about the circumferential axis of the annular ring member variant 110.

Other variants of the annular ring member are depicted in FIGS. 12 to 23. Common to each of the variants of the annular ring member of the present disclosure are the following elements: i) a tine ring; 2) tine driver couplings at a proximal aspect of the tine ring; at least one of a plurality of tines projecting distally from the tine ring, wherein each of the plurality of tines are configured to engage anatomic tissue to axially compress the annular ring member against the anatomic tissue when so engaged.

In all variants of the annular ring member described herein, it is contemplated that the annular ring member may be made out of a wide variety of biocompatible materials, including, without limitation, metals, polymers, composite materials, ceramics, or combinations thereof. The annular ring member may be made of a unitary monolithic material or may be made of the ring, tines, and strain relief components joined together such as by welding. The biocompatible material for the annular ring member may further be a shape memory material, such as a shape memory alloy, e.g., nickel-titanium alloy and the tines may be programmed to have a delivered shape that augments axial compression of the annular ring member against the anatomic tissue. For example, the tines may be programed to have a transition temperature at which the tines evert proximally toward the annular ring member to both aid in axial compression as well as resist pull-out once placed in the anatomic tissue.

Annular ring member variant 120 shown in FIG. 12 includes a tine ring 122, at least one of a plurality of tine driver couplings 124 at a proximal aspect of the tine ring, at least one of a plurality of tines 128 that project distally from the tine ring 122 and may be helically oriented relative to the circumferential axis of the tine ring 122. In variant 120, each of the plurality of tines 126 having a barb 128 proximate to a proximal end of the tine 126 that projects in a direction opposite the tine 126. Further, variant 120 also includes at least one tine ring barb 129 that projects distally from a distal aspect of the tine ring and is positioned intermediate circumferentially adjacent tines 126. Both barb 128 and tine ring barb 129 facilitate anchoring of the annular ring member variant 120 relative to the anatomic tissue when the tines 126 are embedded therein.

Annular ring member variant 130 shown in FIG. 13 includes a tine ring 132, at least one of a plurality of tine driver couplings 134 at a proximal aspect of the tine ring, at least one of a plurality of tines 136 that project distally from the tine ring 132 and may be helically oriented relative to the circumferential axis of the tine ring 132. Each of the at least one of a plurality of tines 136 has a tine head 138 that projects substantially distally along a longitudinal axis of the annular ring member variant 130 and from which the tine 136 then curves to a helical orientation forming angle $\alpha$ between the tine ring 132 and the tine 136. In variant 130, there is also provided a plurality of joining apertures 135 passing laterally through the wall of the tine ring 316. The plurality of joining apertures 135 may be a wide variant of shapes, including, as illustrated in FIG. 13, elongate slots. The plurality of joining apertures 135 may be circumferentially oriented about the tine ring 132 in any of a number of patterns, including a helically oriented array, as illustrated in FIG. 13. The plurality of joining apertures 135 provide an opening through which the tine ring 132 and the tubular graft member 31 may be affixed to one another.

Annular ring member variant 140 shown in FIG. 14 includes a tine ring 142, at least one of a plurality of tine driver couplings 144 at a proximal aspect of the tine ring, at least one of a plurality of tines 148 that project distally from the tine ring 142 and may be helically oriented relative to the circumferential axis of the tine ring 142. In variant 140, each of the plurality of tines 146 having a barb 148 proximate to a proximal end of the tine 146 that projects in a direction opposite the tine 146. Barb 148 facilitates anchoring the annular ring member variant 140 relative to the anatomic tissue when the tines 146 are embedded therein.

FIG. 15 depicts annular ring member variant 150 that includes a tine ring 152, at least one of a plurality of tine driver couplings 154 at a proximal aspect of the tine ring, at least one of a plurality of tines 156 that project distally from the tine ring 152 and may be helically oriented relative to the circumferential axis of the tine ring 152. In this variant 150, at least some of the plurality of tines 156 have a distally oriented curvature along their longitudinal axis. Each of the at least one of a plurality of tines 156 has a tine head 158 that projects substantially distally along a longitudinal axis of the annular ring member variant 150 and from which the tine 156 then curves to a helical orientation forming angle $\alpha$ between the tine ring 152 and the tine 156. As noted above, the plurality of tine driver couplings 154 may consist either of projections from a proximal aspect of the tine ring 152, detents or recesses in a proximal aspect of tine ring 152, or such other structures that are configured to positively and releasably engage with driver engagements 27 on the driver component 24. In variant 150, there is also provided a plurality of joining apertures 155 passing laterally through the wall of the tine ring 152, circumferentially oriented, and arrayed about the circumference of the tine ring 152. The plurality of joining apertures 155 may be a wide variant of shapes, including, for example, elongate slots, geometric through-holes, such as circular, elliptical, oval, or polygonal, curved slots, or wave-form slots. The plurality of joining apertures 155 may be circumferentially oriented about the tine ring 152 in any of a number of patterns, including a helically oriented array, in which there is sufficient open surface area to permit affixation of the tine ring 152 to the tubular graft member 31 (not shown) through the plurality of joining apertures 155.

FIG. 16 depicts annular ring member variant 160 that includes a tine ring 162, at least one of a plurality of tine driver couplings 164 at a proximal aspect of the tine ring 162, at least one of a plurality of tines 166 that project distally from the tine ring 162 and may be helically oriented relative to the circumferential axis of the tine ring 162. In this variant 160, at least some of the plurality of tines 166 have a proximally oriented curvature along their longitudinal axis. The plurality of tine driver couplings 164 may consist either of projections from a proximal aspect of the tine ring 162, detents or recesses in a proximal aspect of tine ring 162, or such other structures that are configured to positively and releasably engage with driver engagements 27 on the driver component 24. Like with annular ring member variant 150, annular ring member variant 160 also has a plurality of joining apertures 165 passing laterally through the wall of the tine ring 162. The plurality of joining apertures 165 may be a wide variant of shapes, including, for example, elongate slots, geometric through-holes, such as circular, elliptical, oval, or polygonal, curved slots, or wave-form slots. The plurality of joining apertures 165 may be circumferentially oriented about the tine ring 162 in any of a number of patterns, including a helically oriented array, in which there is sufficient open surface area to permit affixation of the tine ring 162 to the tubular graft member 31 (not shown) through the plurality of joining apertures 165.

Annular ring variant 170 is depicted in FIG. 17. According to annular ring variant 170, it includes a tine ring 172, at least one of a plurality of tine driver couplings 174 at a proximal aspect of the tine ring 172, at least one of a plurality of tines 176 that project distally from the tine ring 172 and may be helically oriented relative to the circumferential axis of the tine ring 172. At least some of the plurality of tines 176 have a narrowing taper along a length of the tines 176 and the tines are substantially elongate and linear along a substantial aspect of their longitudinal axis. Each of the at least one of a plurality of tines 176 has a tine head 178 that projects substantially distally along a longitudinal axis of the annular ring member variant 170 and from which the tine 176 then curves to a helical orientation forming angle α between the tine ring 172 and the tine 176. The plurality of tine driver couplings 174 may consist either of projections from a proximal aspect of the tine ring 172, detents or recesses in a proximal aspect of tine ring 172, or such other structures that are configured to positively and releasably engage with driver engagements 27 on the driver component 24. Like with annular ring member variants 150 and 160 described above, annular ring member variant 170 also has a plurality of joining apertures 175 passing laterally through the wall of the tine ring 172. The plurality of joining apertures 175 may be a wide variant of shapes, including, for example, elongate slots, geometric through-holes, such as circular, elliptical, oval, or polygonal, curved slots, or wave-form slots. The plurality of joining apertures 175 may be circumferentially oriented about the tine ring 172 in any of a number of patterns, including a helically oriented array, in which there is sufficient open surface area to permit affixation of the tine ring 172 to the tubular graft member 31 (not shown) through the plurality of joining apertures 175.

FIG. 18 illustrates annular ring variant 180, which, like the prior described variants, includes a tine ring 182, at least one of a plurality of tine driver couplings 184 at a proximal aspect of the tine ring 182, at least one of a plurality of tines 186 that project distally from the tine ring 182 and are helically oriented relative to the circumferential axis of the tine ring 182. At least some of the plurality of tines 186 have a narrowing taper along a length of the tines 186 and the tines are substantially elongate and linear along a substantial aspect of their longitudinal axis. Each of the at least one of a plurality of tines 186 has projects distally from the tine ring 182 and has a substantially linear profile along its longitudinal axis and curves to a helical orientation forming angle α between the tine ring 182 and the tine 186. As with other variants, the plurality of tine driver couplings 184 may consist either of projections from a proximal aspect of the tine ring 182, detents or recesses in a proximal aspect of tine ring 182, or such other structures that are configured to positively and releasably engage with driver engagements 27 on the driver component 24. Like with annular ring member variants 150, 160, and 170, described above, annular ring member variant 180 also has a plurality of joining apertures 185 passing laterally through the wall of the tine ring 182. The plurality of joining apertures 185 may be a wide variant of shapes, including, for example, elongate slots, geometric through-holes, such as circular, elliptical, oval, or polygonal, curved slots, or wave-form slots. The plurality of joining apertures 185 may be circumferentially oriented about the tine ring 182 in any of a number of patterns, including a helically oriented array, in which there is sufficient open surface area to permit affixation of the tine ring 182 to the tubular graft member 31 (not shown) through the plurality of joining apertures 185.

FIG. 19 illustrates another variant of the annular ring member 190, which fully depicts the structure of annular ring member variant 110 of FIG. 11. Annular ring member variant 190, like annular ring member variant 110, consists of a tine ring 192, a plurality of tines 196 projecting from a distal aspect of the tine ring 192, and a plurality of tine driver couplings 194 positioned at a proximal aspect of the tine ring 192. In annular ring member variant 190, the tine rings 196 are helically oriented about a circumferential aspect of the tine ring 192. At least some of the tines 196 may, optionally, have a tine aperture 197 passing through the tine 196. Where provided, the tine aperture 197 may be elongated and serve to modulate the elasticity of each tine 196 with which the tine aperture is associated. Alternatively, where provided, the tine aperture 197 may serve as an additional coupling point for joining the annular ring variant 190 to the tubular graft component 31. Annular ring member variant 190 also includes a joining aperture 195 passing laterally through at least some of the plurality of tine driver couplings 194. The joining apertures 195 may also serve as coupling points for joining the annular ring variant 190 to the tubular graft component 31. Finally, tine strain relief members 199 may optionally be provided that interconnect circumferentially adjacent tines 196. Tine strain relief members 199 will allow circumferentially adjacent tines 196 a degree of flexion relative to one another as well as stabilize the tines 196 in a circumferential curvature about the circumferential axis of the annular ring member variant 190.

Figures 20, 21, 22, 23:
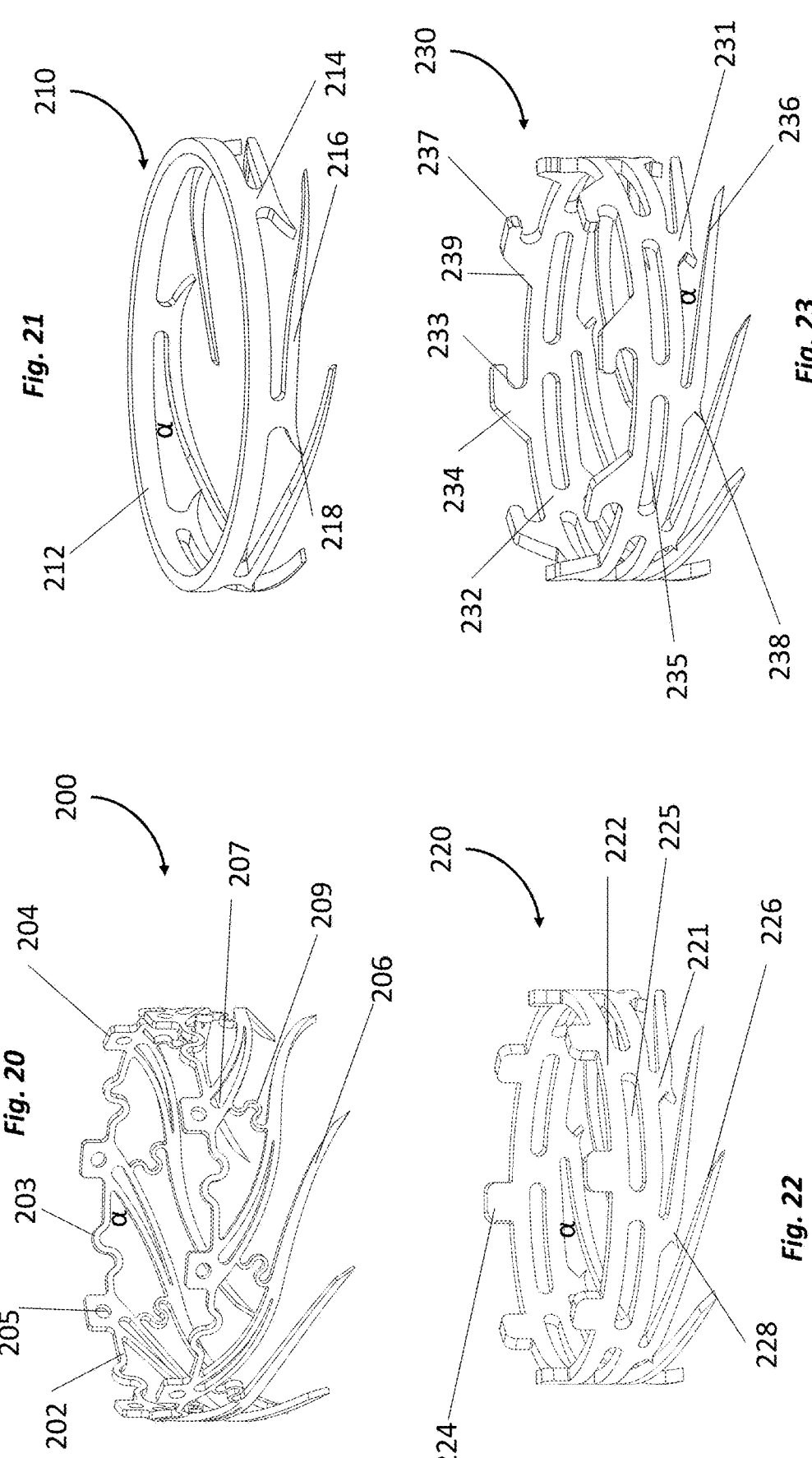
FIG. 20 is a perspective diagrammatic view of a ninth variant of an attachment device in accordance with the present invention.
FIG. 21 is a perspective diagrammatic view of a tenth variant of an attachment device in accordance with the present invention.
FIG. 22 is a perspective diagrammatic view of an eleventh variant of an attachment device in accordance with the present invention.
FIG. 23 is a perspective diagrammatic view of a twelfth variant of an attachment device in accordance with the present invention.

Annular ring member variant 200 is depicted in FIG. 20. Like annular ring member 190, annular ring member variant 200 consists of a tine ring 202, a plurality of tines 206 projecting from a distal aspect of the tine ring 202, and a plurality of tine driver couplings 204 positioned at a proximal aspect of the tine ring 202. Unlike annular ring member variant 190, however, tine ring 202 also has at least one ring strain relief section 203 in the tine ring 202 that is positioned between circumferentially adjacent tine driver couplings 204. The at least one ring strain relief sections affords a degree of radial or diametric expandability to the tine ring 202 as well as a degree of in and out of plane flexibility for the tin ring 202. In annular ring member variant 200, the tines 206 are helically oriented about a circumferential aspect of the tine ring 202. At least some of the tines 206 may, optionally, have a tine aperture 207 passing laterally through the tine 206. Where provided, the tine aperture 207 may be elongated and serve to modulate the elasticity of each tine 206 with which the tine aperture is associated and/or provide an additional coupling point for joining the annular ring variant 190 to the tubular graft component 31. Annular ring member variant 200 also includes a joining aperture 205 passing laterally through at least some of the plurality of tine driver couplings 204 that serve as coupling points for joining the annular ring variant 200 to the tubular graft component 31. Finally, tine strain relief members 209 may optionally be provided which interconnect circumferentially adjacent tines 206. Tine strain relief members 209 will allow circumferentially adjacent tines 206 a degree of flexion relative to one another as well as stabilize the tines 206 in a circumferential curvature about the circumferential axis of the annular ring member variant 200.

Annular ring member variant 210 shown in FIG. 21 includes a tine ring 212, at least one of a plurality of tines 216 that project distally from the tine ring 212 and are helically oriented relative to the circumferential axis of the tine ring 212. In variant 210, each of the plurality of tines 216 have a barb 218 that extends from a proximal end of the barb 216 in an opposite direction to the tine 216. Barb 218 facilitates anchoring the annular ring member variant 210 relative to the anatomic tissue 6 when the tines 216 are embedded therein and prevents counter-rotation and dislodging of the tines 216 from the anatomic tissue 6. Each of the at least one of a plurality of tines 216 has a tine head 214 that projects axially and distally from a distal aspect of the tine ring 212 and is contiguous with the proximal aspect of each of the plurality of tines 216. Each tine then extends circumferentially and distally from the tine head 214 forming angle α between the tine ring 212 and the respective tine 216. Each of the plurality of tines 216 are tapered along their longitudinal axis to a distal point to facilitate penetration and embedding into the anatomic tissue 6.

FIG. 22 illustrates annular ring variant 220, which, like the prior described variants, includes a tine ring 222, at least one of a plurality of tine driver couplings 224 at a proximal aspect of the tine ring 222, at least one of a plurality of tines 226 that project distally from the tine ring 222 and may, optionally, be helically oriented relative to the circumferential axis of the tine ring 222 or may be oriented more longitudinally relative to a longitudinal axis of the tine ring 222. At least some of the plurality of tines 226 have a narrowing taper along a length of the tines 226 and the tines are substantially elongate and linear along a substantial aspect of their longitudinal axis. Each of the at least one of a plurality of tines 226 has projects distally from the tine ring 222 and has a substantially linear profile along its longitudinal axis and curves to a helical orientation forming angle α between the tine ring 222 and the tine 226. In variant 220, each of the plurality of tines 226 have a barb 228 that extends from a proximal end of the barb 226 in an opposite direction to the tine 226. Barb 228 facilitates anchoring the annular ring member variant 220 relative to the anatomic tissue 6 when the tines 226 are embedded therein and restricts counter-rotation and dislodging of the tines 226 from the anatomic tissue 6. Each of the at least one of a plurality of tines 226 has a tine head 221 that projects axially and distally from a distal aspect of the tine ring 222 and is contiguous with the proximal aspect of each of the plurality of tines 226. As with other variants, the plurality of tine driver couplings 224 may consist either of projections from a proximal aspect of the tine ring 222, detents or recesses in a proximal aspect of tine ring 222, or such other structures that are configured to positively and releasably engage with driver engagements 27 on the driver component 24. Like some prior described annular ring member variants, annular ring member variant 220 also has a plurality of joining apertures 225 passing laterally through the wall of the tine ring 222. The plurality of joining apertures 225 may be a wide variant of shapes, including, for example, elongate slots, geometric through-holes, such as circular, elliptical, oval, or polygonal, curved slots, or wave-form slots. The plurality of joining apertures 225 may be circumferentially oriented about the tine ring 222 in any of a number of patterns, including a helically oriented array or an aligned linear array as illustrated in FIG. 22, in which there is sufficient open surface area to permit affixation of the tine ring 222 to the tubular graft member 31 (not shown) through the plurality of joining apertures 225.

Annular ring member variant 230 is illustrated in FIG. 23. Similar to variant 220 of FIG. 22, annular ring member variant 230 includes a tine ring 232, at least one of a plurality of tine driver couplings 234 at a proximal aspect of the tine ring 232, at least one of a plurality of tines 236 that project distally from the tine ring 232 and are helically oriented relative to the longitudinal axis and the circumferential axis of the tine ring 232. At least some of the plurality of tines 236 have a narrowing taper along a length of the tines 236 and the tines are substantially elongate and linear along a substantial aspect of their longitudinal axis. Each of the at least one of a plurality of tines 236 has projects distally from the tine ring 232 and has a substantially linear profile along its longitudinal axis and curves to a helical orientation forming angle α between the tine ring 232 and the tine 236. In variant 230, at least some of the plurality of tines 236 have a barb 238 that extends from a proximal end of the barb 236 in an opposite direction to the direction in which tine 236 projects. Barb 238 facilitates anchoring the annular ring member variant 230 relative to the anatomic tissue 6 when the tines 236 are embedded therein and restricts counter-rotation and dislodging of the tines 236 from the anatomic tissue 6. Each of the at least one of a plurality of tines 236 has a tine head 231 that projects axially and distally from a distal aspect of the tine ring 232 and is contiguous with the proximal aspect of each of the plurality of tines 236. Unlike annular ring member variant 220, at least some of the plurality of tine driver couplings 234 are configured such that each tine driver coupling 234 has an engagement recess 233 on a first circumferential aspect of the tine driver coupling 234, and a sloped wall surface 239 on a second circumferential aspect of the tine driver coupling 234; the first circumferential aspect and the second circumferential aspects of the tine driver coupling 234 are on opposite circumferential surfaces of the tine driver coupling 234. The engagement recess 233 forms a proximally adjacent engagement projection 237, thereby forming a tine driver coupling 234 in which the engagement projection 237 and the engagement recess 233 positively engage corresponding mating driver engagements 27 on the driver component 24. It will be appreciated by those skilled in the art that the tine driver engagements 234 may also be formed as recesses or detents in the proximal surface of the tine ring 232 and have a similar configuration as described above to achieve positive mating with the driver engagements 27 of the driver component 24. The plurality of joining apertures 234 may be a wide variant of shapes, including, for example, elongate slots, geometric through-holes, such as circular, elliptical, oval, or polygonal, curved slots, or wave-form slots. The plurality of joining apertures 235 may be circumferentially oriented about the tine ring 232 in any of a number of patterns, including a helically oriented array or an aligned linear array as illustrated in FIG. 23, in which there is sufficient open surface area to permit affixation of the tine ring 235 to the tubular graft member 31 (not shown) through the plurality of joining apertures 235.

It will be appreciated that with any of the variants 100 to 230 of the annular ring member, where the tines are helically oriented relative to the circumferential and longitudinal axis of the annular ring member, that an angle α between a distal surface of the tine ring 42 and a proximal surface of a tine 46 is formed. Angle α is preferably between about 5 degrees and about 45 degrees to ensure that the plurality of tines 46 gain sufficient purchase in the anatomic tissue 6 to maintain axial compression with the anatomic tissue 6 and resist pull-out. Generally, for a tine 46 of a given length, a larger angle α may be employed to provide faster engagement and reduce the degree of rotation needed to fully engage the plurality of tines 46 with the anatomic tissue 6. It will also be appreciated that where the plurality of tines are helically oriented, the helical orientation may be in a generally clockwise or counterclockwise direction relative to the longitudinal axis of the annular ring member.

Further in any of the variants 110 to 230 of the annular ring member, the tines may have either a distal or a proximal curvature along a longitudinal axis of each of the tine. Alternatively, each of the tines may have a wave-form curvature that has an overall proximal or distal curvature along the longitudinal axis of each tine. For purposes of clarity, it is intended that reference to a distal curvature or a proximal curvature along the longitudinal axis of each tine means that the longitudinal curvature of a tine is oriented either towards a distal or a proximal aspect of the annular ring member, respectively. Moreover, the tines will have a circumferential curvature that approximates to the radius of the tine ring about the circumferential axis of the tine ring. Thus, each of the circumferential and longitudinal curvatures of the plurality of tines facilitates secure embedding of the tines in a manner that resists pull-out or counter-rotation and dislodging of the tines from the anatomic tissue.

Moreover, in all variants of the annular ring member, the plurality of tine driver couplings may consist either of projections from a proximal aspect of the tine ring, detents or recesses in a proximal aspect of tine ring, or such other structures that are configured to positively and releasably engage with driver engagements 27 on the driver component 24.

Figure 25:
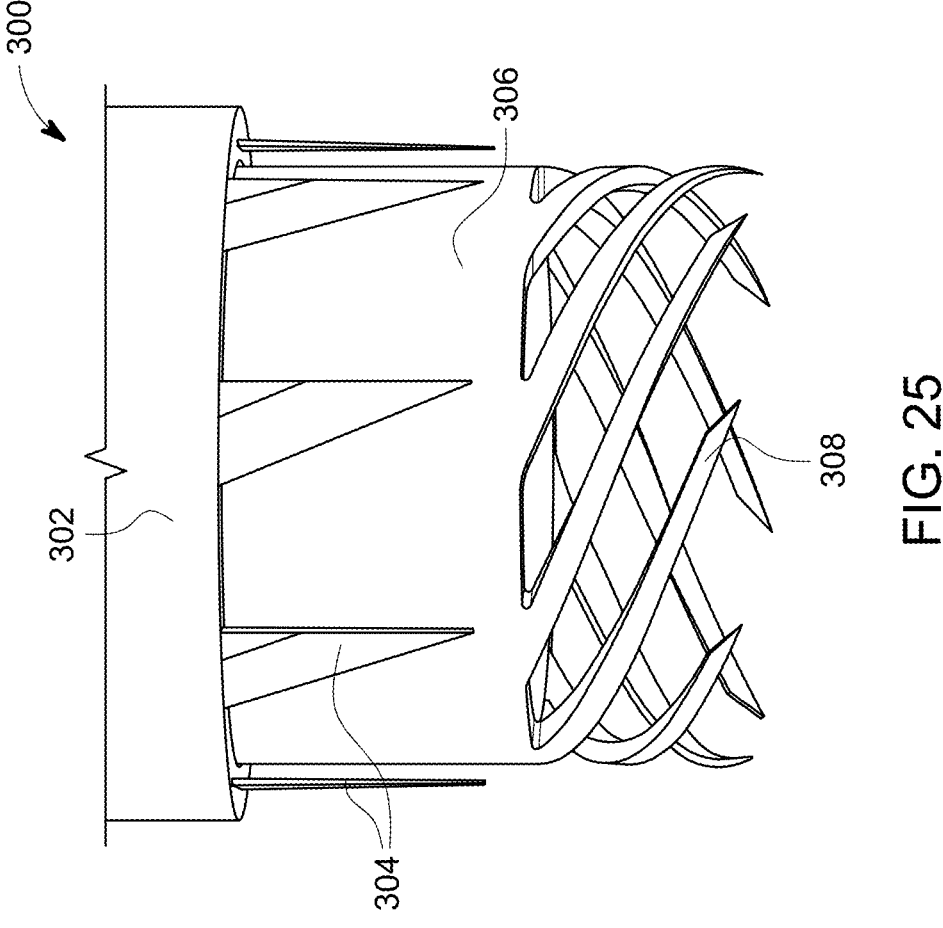
FIG. 25 is a side elevational diagrammatic view of a distal end of the stabilization component and coring component in accordance with a variant of the present invention.

As previously discussed with reference to FIGS. 2A, 2B and 3, a distal end 300 of coring assembly 8 is shown in more detail with reference to FIGS. 24 and 25, the distal end 300 of the coring assembly 8 is shown. The coring knife retention ring 302 fixedly retains at least one of a plurality of coring knives 304 that project distally from the coring knife retention ring 302. The at least one of a plurality of coring knives 304 may be a cylindrical knife similar to a biopsy punch or may be one or more elongated blades having a sharpened surface on at least one surface. The at least one of a plurality of coring knives 304 are in a radially spaced apart relationship relative to stabilization housing 306 and the stabilization tines 308. In this manner, once the stabilization tines 308 are engaged with the anatomic tissue, the at least one of a plurality of coring knives 304 may be longitudinally translated relative to the stabilization tines 308 and stabilization housing 306 to engage the anatomic tissue. The at least one of a plurality of coring knives 304 may then be rotated about their longitudinal axis within the anatomic tissue to cut a cored tissue plug 7 from the anatomic tissue. The cored tissue plug 7 will be securely retained on the plurality of tines 308 and may be removed in conjunction with removal of the entire coring assembly 8.

Figure 28:
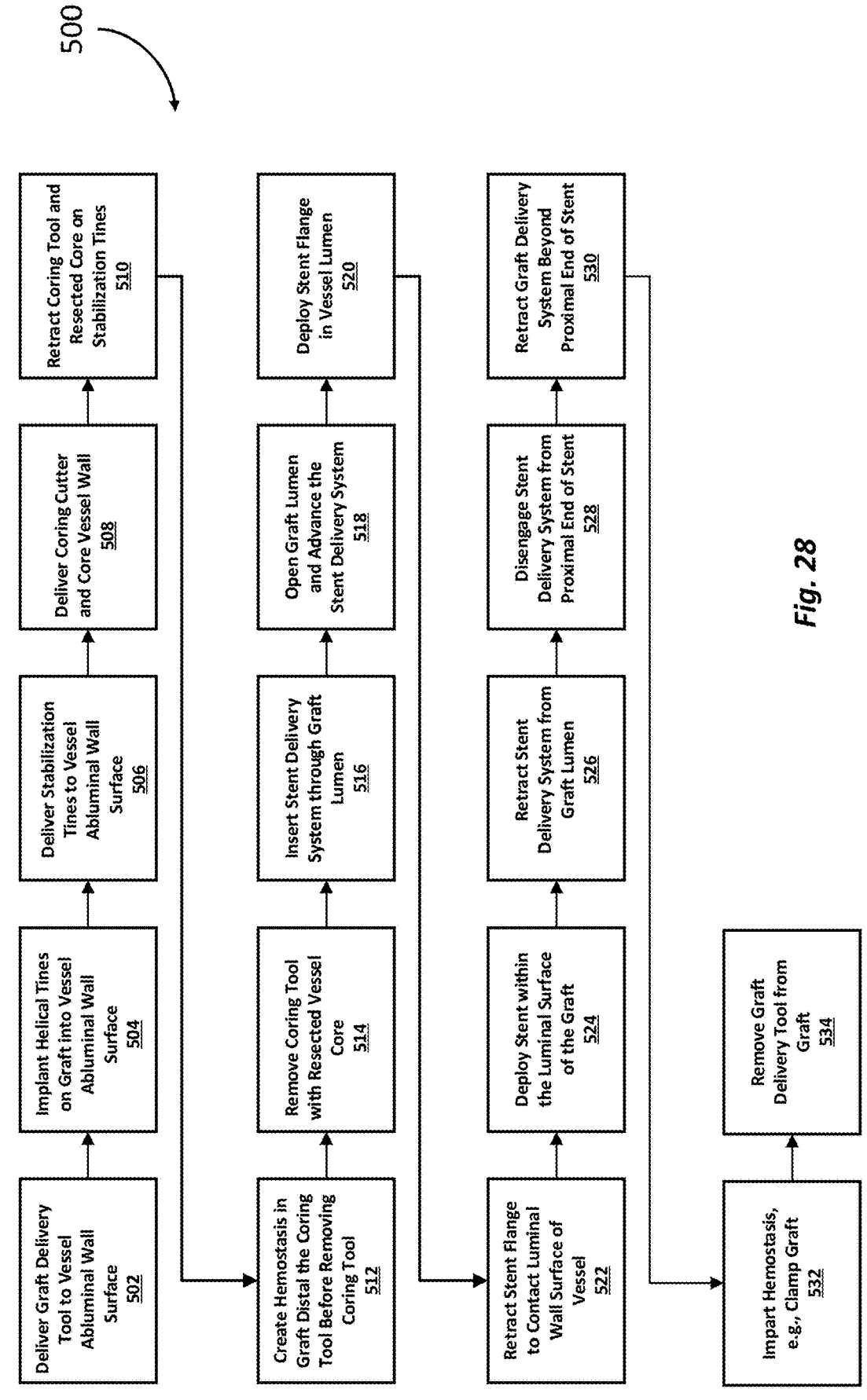
FIG. 28 is a process flow diagram illustrating the methods depicted in FIGS. 26A to 27H.

Turning now to the method of creating the end-to-side connection 400, FIGS. 26A to 27H diagrammatically depict the method steps involved in creating the end-to-side con-nection 400 employing the above-described assembly 10 and its variants. FIG. 28 is a flow chart setting for the sequential method steps 500 corresponding to the method for creating the end-to-side connection 400.

In method 400, the assembly is first engaged onto ana-tomic tissue by placing the distal end of the assembly against the anatomic tissue, the anatomic tissue is axially com-pressed with the axial compression component, and then the tine ring and the at least one of a plurality of tines are engaged to the anatomic tissue 410. The tine ring and tines may be engaged by rotating the driver component to drive the tines into the anatomic tissue and secure the tine ring and graft component to the anatomic tissue. Next, the stabiliza-tion component is longitudinally translated within the lumen of the tubular graft member until the stabilization tines are engaged with the anatomic tissue 412. The at least one of a plurality of coring knives are then translated relative to the stabilization housing and stabilization tines to penetrate into the anatomic tissue 414 and the coring knives rotated to cut a cored tissue plug 416. The entire coring assembly is then translated proximally within the lumen of the tubular graft member, allowing blood or other fluids to partially fill the lumen of the coring assembly and without completely removing the coring assembly 418. The lumen of the tubular graft member is then occluded 420, such as by clamping or cinching the tubular graft member, distal to the cored tissue plug. Thereafter the coring assembly is completely removed from the lumen of the tubular graft member while the distal end of the tubular graft member remains occluded 422.

Next, the stent having a distal flange is delivered into the lumen of the tubular graft member while the distal end of the tubular graft member remains occluded 424. The proximal end of the stent is occluded by the stent delivery system. The occlusion of the tubular graft member is then removed and the distal end of the stent having the distal flange is advanced distally until the distal portion of the stent is positioned with the anatomic tissue, such as within an anatomic passageway 426. Thereafter, the distal flange of the stent is deployed 428, and the stent translated proximally until the distal flange of the stent nests against and abuts the anatomic tissue, such as a luminal wall of an anatomic passageway 430. Once the distal flange of the stent is seated, the proximal portion of the stent is deployed within the distal portion of the lumen of the tubular graft member 432 such that it nests and abuts against a luminal wall surface of the tubular graft member and the stent is then disengaged from the stent delivery system while maintaining hemostasis or fluid sealing within the lumen of the tubular graft member 434. The graft delivery system and the stent delivery system are then translated proximally exposing the tubular graft member and the end-to-side connection with the anatomic tissue, and the lumen of the tubular graft member is then again occluded, such as by clamping or cinching of the tubular graft member 436. Thereafter, the entire graft delivery system and stent deliv-ery system may be completely removed 438. It will be understood that the graft occlusion should be maintained until the proximal end of the tubular graft member is coupled to another device, such as a fluid conduit or pump, to provide fluid inflow into the tubular graft member and the end-to-side connection.

The sequential method steps set forth in FIG. 28 reference the method 500 of creating an end-to-side connection with anatomic tissue having an anatomic passageway, such as a blood vessel. First, the graft delivery system is delivered to an abluminal wall surface of the blood vessel 502. The helical tines on the tine ring coupled to the tubular graft member are then implanted or engaged into the abluminal wall blood vessel 504. Once the helical tines, tine ring, and tubular graft member are so engaged, the stabilization component is delivered to the abluminal wall surface and the stabilization tines engaged with the anatomic tissue of the abluminal wall of the blood vessel 506. Once the stabilization component is secured with the anatomic tissue, the coring component is engaged with the blood vessel and the vessel wall is cored about the stabilization tines such that the stabilization tines retain the cored tissue plug thereupon 508. The coring tool, cored tissue plug, and stabilization component are then retracted proximally, but not removed 510. Thereafter, hemostasis is created distal to the retracted coring tool, cored tissue plug, and stabilization component, such as by clamping or other occlusion of the tubular graft lumen 512. Once the tubular graft lumen is occluded, the coring tool, cored tissue plug, and stabilization component are fully removed from within the tubular graft lumen proximal to the occlusion 514.

The stent delivery system is then delivered through the tubular graft lumen and proximal to the occlusion 516, thereafter, the occlusion is removed to open the graft lumen and the stent delivery system is advanced into the cored opening in the blood vessel 518. The distal stent flange is deployed within the blood vessel lumen 520, and the stent is then retracted proximally to abut the distal flange of the stent against the luminal wall surface of the blood vessel 522. Once the stent flange is positioned against the luminal wall surface of the blood vessel, the proximal portion of the stent is then deployed within the lumen of the tubular graft member 524. The stent delivery system is then retracted proximally within the tubular graft lumen 526 and the stent disengaged from the stent delivery system 528. Once the stent is disengaged from the stent delivery system, the stent delivery system is retracted further within the lumen of the tubular graft member, but not fully removed from the graft lumen 530 and hemostasis is imparted, such as by clamping or cinching the graft lumen between the stent delivery system and the proximal end of the stent 532. Once hemostasis is achieved, the stent delivery system may be removed completely from the graft lumen 534 and the graft lumen maintained hemostatically until the proximal end of the tubular graft member is coupled to another conduit or device.

Once the end-to-side connection is made, such as with a major vessel, the output from a VAD pump or other fluid source, will be coupled to the proximal end of the tubular graft member. It will be understood that the output from a VAD pump or other fluid source may, itself, be an anatomic passageway or may be an exogenous conduit such as a surgical graft that conveys fluid into the proximal end of the tubular graft member of the end-to-side connection. The connection between the output from a VAD pump or other fluid source may be made by joining to the proximal end of the tubular graft member and securing it in a hemostatic manner by any of a wide variety of hemostatic securements. Examples of suitable hemostatic securements include, for example, a suture ligature, a circumferential cinch, a circumferential clamp, barb fittings, or other hemostatic fittings, or the like. It is important, however, that the hemostatic securement does not constrict or impede patency of the lumen of the tubular graft member or the stent.

It will be understood that the various embodiments described above are intended to be interchangeable with one another. For example, the configuration or orientation of the tine ring, the tines projecting distally from the tine ring, the configuration or orientation of the coring knife or knives, the configuration or orientation of the stabilization tines, the configuration or orientation of the tine ring engagements, as described above with respect to the various embodiments thereof are all intended to be and considered to be interchangeable with one another. Accordingly, the embodiments are not intended to be limited to the specific embodiments depicted in the accompanying Figures but may exchange or substitute components from other embodiments of assembly 10 or its various components.

As noted above, the variants of end-to-side anastomosis assembly 10, 60, and/or 100 may also be used in a wide variety of non-vascular medical applications to create end-to-side conduits between anatomic passageways or between a tubular conduit and an anatomic passageway. Those skilled in the art will appreciate and understand that the scope of utility and the scope of the constructs of the end-to-side assemblies of the present disclosure described herein may have a large number of variations and that the scope of the invention is limited only by the claims appended hereto.

The invention claimed is:

1. A tissue connection device, comprising an annular ring having a plurality of helically oriented tines, each of the plurality of helically oriented tines projecting axially and distally from a distal end of the annular ring, each of the plurality of tines are configured to penetrate directly into and be retained in anatomical tissue, and a plurality of axial projections extending from a proximal end of the annular ring, each of the axial projections being configured to removably couple to a delivery device and circumferentially rotate the annular ring to drive the plurality of helically oriented tines directly into the anatomical tissue, and a tubular graft member coupled to an inner circumference of the annular ring, wherein the plurality of helically oriented tines extend beyond and circumferentially surround a distal end of the tubular graft member.

2. The tissue connection device according to claim 1, further comprising a stent coupled to the annular ring and/or the tubular graft member.

3. The tissue connection device according to claim 1, wherein the plurality of tines is helically oriented relative to a longitudinal axis of the annular ring.

4. The tissue connection device according to claim 3, wherein at least some of the plurality of helically oriented tines have at least one barb projecting from a proximal end thereof and extending in a direction opposite the projection of the tine with which it is associated.

5. The tissue connection device according to claim 1, wherein the plurality of helically oriented tines are each configured to penetrate into the anatomical tissue and extend to abut with an inner surface of the anatomical tissue and axially compress the anatomical tissue between the annular ring and the plurality of helically oriented tines.

6. The tissue connection device according claim 5, further comprising a graft delivery tool, the graft delivery tool comprising an axial compression sleeve having a plurality of projections from a distal end of the axial compression sleeve and a handle at a proximal end of the axial compression sleeve, the axial compression sleeve having an inner diameter that accommodates the tubular graft member concentrically within the axial compression sleeve.

7. The tissue connection device according to claim 6, further comprising a driver tool, the driver tool comprising a tubular member having a plurality of engagement sections at a distal end of the tubular member and a handle at a proximal end of the tubular member, the tubular member being configured to be concentrically positioned between the axial compression sleeve and the tubular graft member and removably engage with the annular ring.

8. The tissue connection device according to claim 7, wherein the plurality of engagement sections removably engage with the plurality of axial projections extending from the proximal end of the annular ring arrayed about a circumference of the annular ring.

9. The tissue anastomosis device according to claim 7, further comprising a coring tool, the coring tool further comprising a stabilization member and a tissue core cutting member concentrically engaged with each other.

10. The tissue connection device according to claim 9, wherein the stabilization member further comprises an elongate tubular member having a plurality of stabilization tines helically projecting from a distal end of the elongate tubular member and a handle.

11. The tissue connection device according to claim 10, wherein the plurality of stabilization tines project in a circumferential direction opposite the plurality of tines on the annular ring member.

12. The tissue connection device according to claim 10, wherein the tissue core cutting member further comprises a tubular cutting member having at least one of a plurality of tissue knives projecting from a distal end of the tubular cutting member and a handle, the tubular cutting member configured to concentrically engage with the elongate tubular member of the stabilization member and be independently movable relative thereto.

13. A tissue connection device capable of being joined to anatomical tissue, comprising an annular ring having a plurality of tines helically projecting axially and distally from a distal end of the annular ring, a plurality of projections or a plurality of recesses in a proximal end of the annular ring configured to engage with an annular ring driver, and a tubular graft member affixed concentrically to an inner circumference of the annular ring, and having a distal end of the tubular graft member projecting axially and distally from the distal end of the annular ring such that the plurality of tines extend beyond and circumferentially surround the distal end of the tubular graft member, and the distal end of the tubular graft member is configured to engage with an inner surface of an opening in the anatomical tissue and the plurality of tines are configured to directly engage and embed into the anatomical tissue.

14. The tissue connection device of claim 13, wherein each of the plurality of tines further comprise a distal taper.

15. The tissue connection device of claim 13, wherein each of the plurality of tines further have a transverse cross-sectional profile configured to compress and/or seal the anatomical tissue.

* * * * *